United States Patent [19]

Breuer et al.

[11] Patent Number: 4,670,553
[45] Date of Patent: Jun. 2, 1987

[54] 2-OXO-1-(AMINOCARBONYLAMINOSULFONYL-AMINOCARBONYL)AZETIDINES

[75] Inventors: Hermann Breuer, Schoenhofen; Theodor Denzel, Regensburg, both of Fed. Rep. of Germany

[73] Assignee: E. R. Squibb & Sons, Inc., Princeton, N.J.

[21] Appl. No.: 444,771

[22] Filed: Nov. 26, 1982

Related U.S. Application Data

[63] Continuation-in-part of Ser. No. 336,537, Jan. 4, 1982, abandoned, and Ser. No. 368,609, Apr. 15, 1982, abandoned.

[51] Int. Cl.⁴ ............... C07D 205/08; C07D 401/12; C07D 417/12; A61K 31/395
[52] U.S. Cl. .................... 540/363; 540/357; 540/360; 540/364
[58] Field of Search ............ 260/239 A, 245.4; 540/357, 360, 363, 364

[56] References Cited

U.S. PATENT DOCUMENTS 4,581,170 4/1986 Mueller .................... 540/355

Primary Examiner—Mark L. Berch
Attorney, Agent, or Firm—Lawrence S. Levinson; Donald J. Barrack

[57] ABSTRACT

Antibacterial activity is exhibited by compounds having the formula

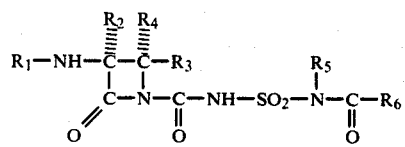

and salts thereof, wherein
$R_1$ is acyl;
$R_2$ is hydrogen or methoxy;
$R_3$ and $R_4$ are the same or different and each is hydrogen, alkyl, alkenyl, alkynyl, cycloalkyl, aryl or a 5,6 or 7-membered heterocycle or one of $R_3$ and $R_4$ is hydrogen and the other is azido, halomethyl, dihalomethyl, trihalomethyl, alkoxycarbonyl, 2-phenylethenyl, 2-phenylethynyl, carboxyl,

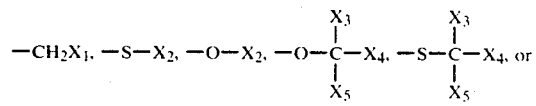

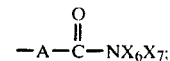

$X_1$ is azido, amino, hydroxy, alkanoylamino, alkylsulfonyloxy, arylsulfonyloxy, aryl, cyano, $-S-X_2$ or $-O-X_2$;

$X_2$ is alkyl, substituted alkyl, aryl, arylalkyl, alkanoyl, substituted alkanoyl, arylcarbonyl or heteroarylcarbonyl;

one of $X_3$ and $X_4$ is hydrogen and the other is hydrogen or alkyl, or $X_3$ and $X_4$ when taken together with the carbon atom to which they are attached from a cycloalkyl group;

$X_5$ is formyl, alkanoyl, arylcarbonyl, arylalkylcarbonyl, carboxyl, alkoxycarbonyl, aminocarbonyl, (substituted amino)carbonyl, or cyano;

A is $-CH=CH-$, $-CH_2-CH=CH-$, $-(CH_2)_m-$, $-(CH_2)_{m'}-O-$, $-(CH_2)_{m'}-NH-$, $-(CH_2)_{m'}-S-CH_2-$, or $-(CH_2)_m-O-CH_2-$;

m is 0, 1, 2 or 3;

m' is 1 or 2;

$X_6$ and $X_7$ are the same or different and each is hydrogen or alkyl, or $X_6$ is hydrogen and $X_7$ is amino, substituted amino, acylamino or alkoxy;

$R_5$ is hydrogen, alkyl or aryl;

$R_6$ is hydrogen, alkyl, aryl, a 5,6 or 7-membered heterocycle, $-NR_7R_8$, or $-(CH_2)_n-X$ wherein n is 1,2,3 or 4 and X is halogen, aryl, alkoxy, aryloxy or $-NR_9R_{10}$;

$R_7$ and $R_8$ are the same or different and each is hydrogen, alkyl or aryl, or $R_7$ is hydrogen and $R_8$ is a 5,6 or 7-membered heterocycle or $-(CH_2)_n-Y$ wherein n is 1,2,3 or 4 and Y is alkoxy, amino, alkylthio or halogen; and $R_9$ and $R_{10}$ are the same or different and each is hydrogen or alkyl, or $R_9$ is hydrogen and $R_{10}$ is a 5,6 or 7-membered heterocycle.

26 Claims, No Drawings

2-OXO-1-(AMINOCARBONYLAMINOSULFONYL-AMINOCARBONYL)AZETIDINES

This application is a coninuation-in-part of U.S. patent application Ser. No. 336,537, filed Jan. 4, 1982, and now abandoned, and of U.S. patent Ser. No. 368,609, filed Apr. 15, 1982, and now abandoned.

RELATED APPLICATIONS

U.S. patent application Ser. No. 252,672, filed Apr. 9, 1981, and now abandoned discloses β-lactam antibiotics having in the 1-position an activating group of the formula

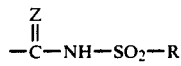

wherein Z is oxygen or sulfur and R is alkyl, alkenyl, alkynyl, substituted alkyl, phenyl, substituted phenyl, heteroaryl, phenylakyl, (substituted phenyl)alkyl, (heteroaryl)alkyl or —NR'R" wherein R' and R" are the same or different and each is hydrogen, alkyl, substituted alkyl, phenyl, substituted phenyl, heteroaryl, phenylalkyl, (substituted phenyl)alkyl, or (heteroaryl)alkyl, or one of R' and R" is hydrogen, alkyl, phenyl or substituted phenyl, and the other is amino, alkanoylamino, alkylamino, dialkylamino, phenylamino, (substituted phenyl)amino, hydroxy, cyano, alkoxy, phenyloxy, (substituted phenyl)oxy, phenylalkoxy, (substituted phenyl)alkoxy, (heteroaryl)alkoxy, alkylmethyleneamino, phenylmethyleneamino, or (substituted phenyl)methyleneamino, or R' and R" together with the nitrogen atom to which they are attached form a 5,6 or 7-membered fully or partially saturated ring optionally containing additional nitrogen, oxygen or sulfur atoms.

BRIEF DESCRIPTION OF THE INVENTIONS

β-Lactams having the formula

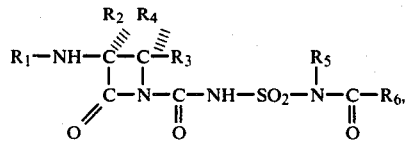

and salts thereof, have antibacterial activity. In formula I, and throughout the specification, the symbols are as defined below.

$R_1$ is acyl;

$R_2$ is hydrogen or methoxy;

$R_3$ and $R_4$ are the same or different and each is hydrogen, alkyl, alkenyl, alkynyl, cycloalkyl, aryl or a 5,6 or 7-membered heterocycle or one of $R_3$ and $R_4$ is hydrogen and the other is azido, halomethyl, dihalomethyl, trihalomethyl, alkoxycarbonyl, 2-phenylethenyl, 2-phenylethynyl, carboxyl, —$CH_2X_1$, —S—$X_2$, —O—$X_2$,

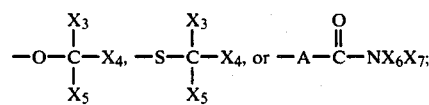

$X_1$ is azido, amino (—$NH_2$), hydroxy, alkanoylamino, alkylsulfonyloxy, arylsulfonyloxy, aryl, cyano, —S—$X_2$ or —O—$X_2$;

$X_2$ is alkyl, substituted alkyl, aryl, arylalkyl, alkanoyl, substituted alkanoyl, arylcarbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, arylcarbonyl, arylalkylcarbonyl, carboxyl, alkoxycarbonyl, aminocarbonyl

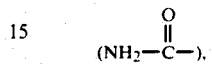

(substituted amino)carbonyl, or cyano (—C≡N);

A is —CH=CH—, —$CH_2$—CH=CH—, —($CH_2$)$_m$, —($CH_2$)$_{m'}$, —O—, —($CH_2$)$_{m'}$, —NH—, —($CH_2$)$_{m'}$, —S—$CH_2$—, or —($CH_2$)$_{m'}$, —O—$CH_2$—;

m is 0, 1, 2 or 3;

m' is 1 or 2;

$X_6$ and $X_7$ are the same or different and each is hydrogen or alkyl, or $X_6$ is hydrogen and $X_7$ is amino, substituted amino, acylamino or alkoxy;

$R_5$ is hydrogen, alkyl or aryl;

$R_6$ is hydrogen, alkyl, aryl, a 5, 6 or 7-membered heterocycle, —$NR_7R_8$, or —($CH_2$)$_n$—X wherein n is 1,2,3 or 4 and X is halogen, aryl, alkoxy, aryloxy or —$NR_9R_{10}$;

$R_7$ and $R_8$ are the same or different and each is hydrogen, alkyl or aryl, or $R_7$ is hydrogen and $R_8$ is a 5,6 or 7-membered heterocycle or —($CH_2$)$_n$—Y wherein n is 1,2,3 or 4 and Y is alkoxy, amino(—$NH_2$), alkylthio or halogen; and $R_9$ and $R_{10}$ are the same or different each is hydrogen or alkyl, or $R_9$ is hydrogen and $R_{10}$ is a 5,6 or 7-membered heterocycle.

Listed below are definitions of various terms used to describe the β-lactams of this invention. These definitions apply to the terms as they are used throughout the specification (unless they are otherwise defined in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The terms "alkanoyl", "alkenyl", "alkynyl", "alken-1-yl" and "alkyn-1-yl" refer to both straight and branched chain groups. Those groups having 2 to 10 carbon atoms are preferred.

The term "halogen" refers to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "aryl" refers to phenyl and phenyl substituted with 1,2 or 3 amino(—$NH_2$), halogen, hydroxyl, trifluoromethyl, alkyl (of 1 to 4 carbon atoms), alkoxy (of 1 to 4 carbon atoms) or carboxyl groups.

The expression "a 5, 6 or 7-membered heterocycle" refers to substituted and unsubstituted, aromatic and non-aromatic groups containing one or more nitrogen, oxygen or sulfur atoms. Exemplary substituents are oxo(=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furylmethyleneimino

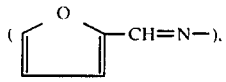

phenylmethyleneimino and substituted alkyl groups (wherein the alkyl group has 1 to 4 carbons). One type of "5,6 or 7-membered heterocycle" is the "heteroaryl" group. The term "heteroaryl" refers to those 5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted piperidinyl, piperazinyl, imidazolidinyl, oxazolidinyl, pyrrolidinyl, tetrahydropyrimidinyl, and dihydrothiazolyl. Exemplary of the substituted 5, 6 or 7-membered heterocycles are 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-aryl-2-oxo-1-imidazolidinyl, 3-(2-hydroxyethyl)-2-oxo-1-imidazolidinyl, 3-[(1-methylethylidene)amino]-2-oxo-1-imidazolidinyl, 3-benzyl-2-oxo-1-imidazolidinyl, 3-(2-aminoethyl)-2-oxo-1-imidazolidinyl, 3-[2-(alkylamino)ethyl]-2-oxo-1-imidazolidinyl, 3-[2-(dialkylamino)ethyl]-2-oxo-1-imidazolidinyl, 3-amino-2-oxo-1-imidazolidinyl, 3-ureido-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1pyrrolidinyl, 2-oxo-3-oxazolidinyl, 4-hydroxy-6-methyl-2-pyrimidinyl, 2-oxo-3-pyrroldinyl, 2-oxo-3-tetrahydrofuranyl, 2,3-dioxo-1-piperazinyl, 2,5-dioxo-1piperazinyl, 4-alkyl-2,3-dioxo-1-piperazinyl, and 4-phenyl-2,3-dioxo-1-piperazinyl.

The term "substituted alkyl" refers to alkyl groups substituted with one, or more, azido, amino(—NH₂), halogen, hydroxy, carboxy, cyano, alkoxycarbonyl, aminocarbonyl, alkanoyloxy, alkoxy, aryloxy, a 5,6 or 7-membered heterocycleoxy, mercapto, alkylthio, arylthio, alkylsulfinyl, or alkylsulfonyl groups.

The term "substituted amino" refers to a group having the formula —NY₁Y₂ wherein Y₁ is hydrogen, alkyl, aryl, or arylalkyl, and Y₂ is alkyl, aryl, arylalkyl, hydroxy, cyano, alkoxy, phenylalkoxy, or amino(—NH₂).

The term "substituted alkanoyl" includes within its scope compounds having the formula

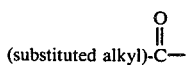

(wherein "substituted alkyl" is defined above) and phenylalkanoyl.

The term "acyl" refers to all organic radicals derived from an organic acid (i.e., a carboxylic acid) by removal of the hydroxyl group. Certain acyl groups are, or course, preferred but this preference should not be viewed as a limitation of the scope of this invention.

Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian patent No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British patent No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

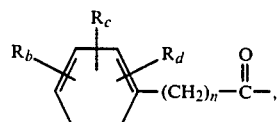

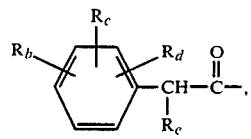

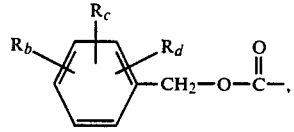

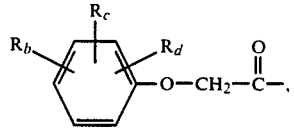

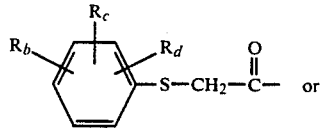 or

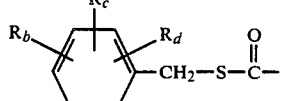

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

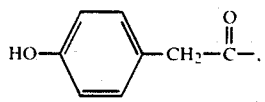

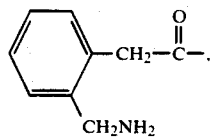

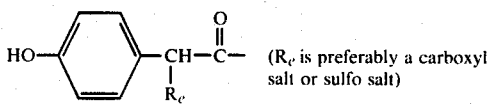  ($R_e$ is preferably a carboxyl salt or sulfo salt)

and

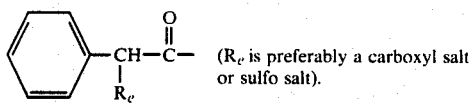  ($R_e$ is preferably a carboxyl salt or sulfo salt).

(c) Heteroaromatic groups having the formula

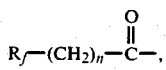

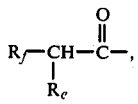

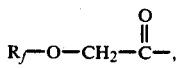

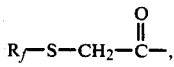

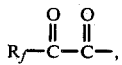

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms, Exemplary heterocyclic rings are thienyl, furyl, pyrrolyl, pyridinyl, pyrazolyl, pyrazinyl, thiazolyl, thiadiazolyl, pyrimidinyl and tetrazolyl. Exemplary substituents are halogen, hydroxyl, nitro, amino, cyano, trifluoromethyl, alkyl of 1 to 4 carbon atoms, alkoxy of 1 to 4 carbon atoms, or

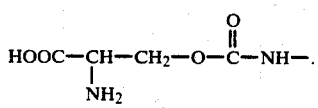

Preferred heteroaromatic acyl groups include those groups of the above formulas wherein $R_f$ is 2-amino-4-thiazolyl, 2-amino 5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

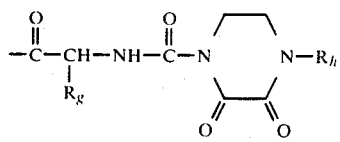

wherein $R_g$ is an aromatic group (including carbocyclic aromatics such as those of the formula

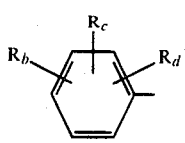

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is as defined above), arylcarbonylamino (i.e.,

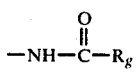

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oxyimino)arylacetyl groups having the formula

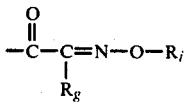

wherein $R_g$ is as defined above and $R_i$ is hydrogen, alkyl, cycloalkyl, alkylaminocarbonyl, arylaminocarbonyl (i.e.,

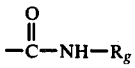

wherein $R_g$ is as defined above) or substituted alkyl (wherein the alkyl group is substituted with 1 or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl or 2,2,2-trifluoroethyl.

(f) (Acylamino)arylacetyl groups having the formula

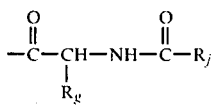

wherein $R_g$ is as defined above and $R_j$ is

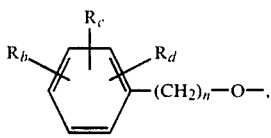

amino, alkylamino, (cyanoalkyl)-amino, amido, alkylamido, (cyanoalkyl)amido,

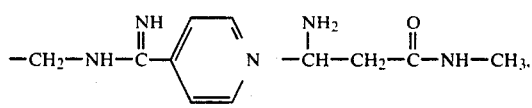

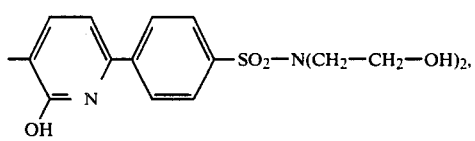

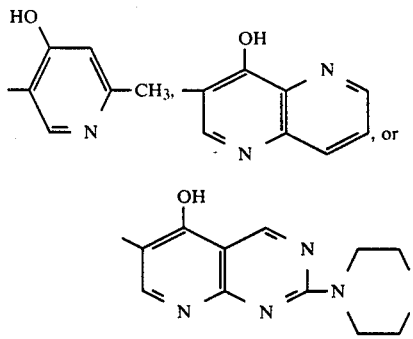

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

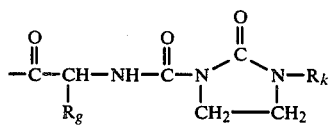

wherein $R_g$ is as defined above and $R_k$ is hydrogen, alkylsulfonyl, arylmethyleneamino (i.e., —N=CH—$R_g$ wherein $R_g$ is defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted- 2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

β-Lactams having a

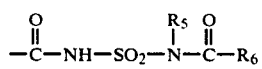

substituent in the 1-position and an acylamino substituent in the 3-position contain at least one chiral center—the carbon atom (in the 3-position of the β-lactam nucleus) to which the acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

Also included within the scope of this invention are racemic mixtures which contain the above-described β-lactams.

DETAILED DESCRIPTION OF THE INVENTION

β-Lactams having a

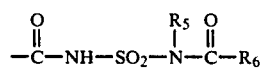

substituent in the 1-position of the β-lactam nucleus and an acylamino substituent in the 3-position of the β-lactam nucleus, and salts thereof, have activity against a range of gram-negative and gram-positive organisms.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

A

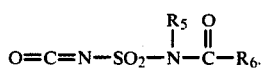

activating group can be introduced onto the nitrogen atom of a β-lactam by reacting a β-lactam having the formula

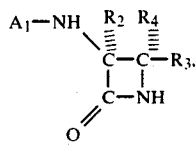    II wherein $A_1$ is a nitrogen protecting group, with the appropriate isocyanate having the formula

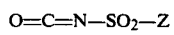    III

The reaction is preferably run in an organic solvent, e.g., an inert solvent such as tetrahydrofuran or dimethoxyethane, in the presence of a base such as triethylamine or alkyl lithium.

An alternative, and preferred route for introducing a substituent onto the nitrogen atom of a β-lactam of formula II comprises first reacting a β-lactam of formula II with an isocyanate having the formula

O=C=N—SO$_2$—Z    IV wherein Z is a leaving group, e.g., a halogen such as chlorine. The reaction is preferably run in an inert organic solvent, e.g., a halocarbon such as dichloromethane, or in acetonitrile, and yields an intermediate having the formula

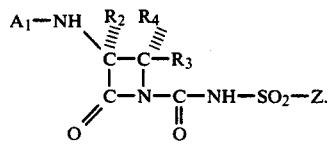    V

Reaction of an intermediate of formula V with a silyl compound having the formula

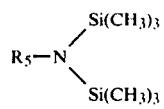    VI yields an intermediate having the formula

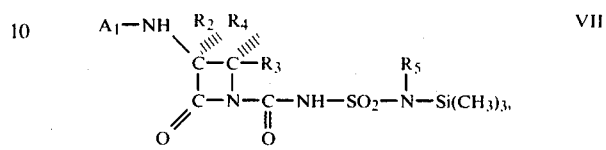    VII which can be reacted with an acyl halide having the formula

    VIII to yield a β-lactam having the formula

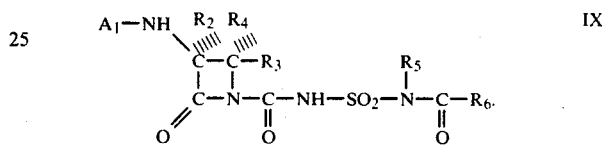    IX

Alternatively, compounds of formulas VI and VIII can be first reacted to yield a compound having the formula

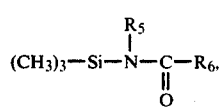    X which can be reacted with a compound of formula V to yield a compound of formula IX.

Still another procedure for preparing a compound of formula IX wherein $R_6$ is —$NR_7R_8$, comprises reacting a compound of formula V with a urea having the formula

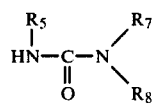    XI in the presence of triethylamine.

Deprotection of a compound of formula IX using conventional techniques yields the corresponding key intermediate having the formula

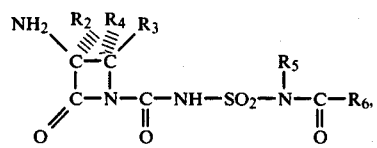    XII or a salt thereof. The particular deprotection reaction used will, of course, depend on the protecting group ("$A_1$") present. If, for example, $A_1$ is a t-butoxycarbonyl protecting group, deprotection can be accomplished by treatment of a compound of formula IX with acid (e.g., formic acid or trifluoroacetic acid). If, for example, $A_1$ is a benzyloxycarbonyl protecting group, deprotection can be accomplished by catalytic hydrogenation of a compound of formula IX.

Well known acylation techniques can be used to convert an intermediate of formula XII to a corresponding product of formula I. Exemplary techniques include reaction of a compound of formula XII with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

The azetidinones of formula II can be prepared utilizing the procedures described in United Kingdom patent application No. 2,071,650, published Sept. 23, 1981.

The preferred compounds of formula I are those wherein $R_3$ and $R_4$ are each hydrogen. Also preferred are those compounds of formula I wherein $R_6$ is a 5,6 or 7-membered heterocycle, especially a 4-alkyl-2,3-dioxo-1-piperazinyl group, a 2-oxo-1-ixidazolidinyl group, a 3-alkyl-2-oxo-1-imidazolidinyl group or a 3-(substituted alkyl)-2-oxo-1-imidazolidinyl group. Specific groups that are preferred are the 4-ethyl-2,3-dioxo-1-piperazinyl, 3-ethyl-2-oxo-1-imidazolidinyl, and 3-(2-aminoethyl)-2-oxo-1-imidazolidinyl groups. Preferred 3-acylamino groups are those wherein the acyl portion of the group is (Z)-2-amino-α-(alkoxyimino)-4-thiazoleacetyl or (Z)-2-amino-[[(substituted alkyl)oxy]imino]-4-thiazoleacetyl, especially (Z)-2-amino-α-(methoxyimino)-4-thiazoleacetyl and (Z)-2-amino-α[[(1-carboxy-1-methylethoxy)imino]-4-thiazoleacetyl.

The following examples are specific embodiments of this invention.

EXAMPLE 1

[3S(Z)]-N-[1-[[[(Acetylamino)sulfonyl]amino]-carbonyl]-2-oxo-3-azetidinyl]-2-amino-α-(methoxyimino)-4-thiazoleacetamide, dipotassium salt (A)

(S)-[1-[[[(Acetylamino)sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (4.4 g) was suspended in dry ethyl acetate. The mixture was cooled to −5° C. and 3.1 g of chlorosulfonyl isocyanate was dropped in with stirring at such a rate that the temperature did not exceed 0° C. Stirring at 0° C. was continued for an additional 20 minutes. After this time 4 g of hexamethyldisilazane was added and the solution was stirred at ambient temperature for 12 hours. Acetyl chloride (3.2 g) was added and the solution was again stirred for 48 hours. The ethyl acetate was then washed with water and extracted twice with 50 ml portions of saturated aqueous bicarbonate. The organic layer was discarded and the aqueous phase was treated with 25% hydrochloric acid until the pH was 1.0. Extraction with ethyl acetate, drying and evaporation of the solvent yielded 4 g of the title compound in crude form. This was dissolved in acetone/water (1:1), the pH was adjusted to 6.5, the solvent was removed in vacuo and the crystalline title compound was filtered off with ether. Further purification achieved by HP-20 chromatography (water/acetone 9:1 as eluent) yielded the title compound, melting point 130°–135° C., dec.

(B) [3S(Z)]-N-[1-[[[(Acetylamino)sulfonyl]amino]carbonyl]-2-oxo-3-azetidinyl]-2-amino-α-(methoxyimino)-4-thiazoleacetamide, dipotassium salt (S)-[1-[[[(Acetylamino)sulfonyl]amino]carbonyl]-2-oxo-3-azetidinyl]carbamic acid, phenylmethyl ester, potassium salt (940 mg) was dissolved in 50 ml of dry dimethylformamide and hydrogenated in the presence of 500 mg of 10% palladium on charcoal for 30 minutes, after which the catalyst was filtered off. (Z)-2-Amino-α-(methoxyimino)-4-thiazoleacetic acid (450 mg), 1 g of dicyclohexylcarbodiimide and 150 mg of N-hydroxybenzotriazole were added to the filtrate. The solution was stirred overnight, the precipitated urea was filtered off and the solvent was removed in vacuo. The remaining solid was chromatographed on HP-20* using water as eluent, and yielded 400 mg of product, melting point 255°–260° C., dec.

*The terms "HP-20" and "HP-20 resin" refer to macroporous styrene-divinylbenzene copolymer.

EXAMPLE 2

[3(Z)]-2-[[[2-[[1-[[[(Acetylamino)sulfonyl]amino]carbonyl]-2-oxo-3-azetidinyl]amino]-1-(2-amino-4-thiazolyl)-2-oxoethylidene]amino]oxy]-2-methylpropanoic acid (A)

2-[[[2-[[1-[[[(Acetylanino)sulfonyl]amino]carbonyl]-2-oxo-3-azetidinyl]amino]-1-(2-amino-4-thiazolyl)-2-oxoethylidene]amino]oxy]-2-methylpropanoic acid, diphenylmethyl ester, monopotassium salt (S)-[1-[[[(Acetylamino)sulfonyl]amino]carbonyl]-2-oxo-3-azetidinyl]carbamic acid, phenylmethyl ester, potassium salt (1.38 g; see example (1A) was hydrogenated in dry dimethylformamide in the presence of 700 mg of 10% palladium on charcoal for 30 minutes after which the catalyst was filtered off. (Z)-2-Amino-α-[[2-(diphenylmethoxy)-1,1-dimethyl-2-oxoethoxy]imino]-4-thiazoleacetic acid (1.32 g), 1.2 g of dicyclohexylcarbodiimide and 150 mg of N-hydroxybenzotriazole were added and the solution was stirred for 12 hours. The precipitated urea was filtered off and the solvent was removed in vacuo. The residue was dissolved in 20 ml of acetone, filtered and poured into 100 ml of ether. The precipitated title compound was filtered off and dried yielding 2.5 g of material.

(B)

[3S(Z)]-2-[[[2-[[1-[[[(Acetylamino)sulfonyl]amino]carbonyl]-2-oxo-3-azetidinyl]amino]-1-(2-amino-4-thiazolyl)-2-oxoethylidene]amino]oxy]-2-methylpropanoic acid 2-[[[2-[[1-[[[(Acetylamino)sulfonyl]amino]carbonyl]-2-oxo-3-azetidinyl]amino]-1-(2-amino4-thiazolyl)-2-oxoethylidene]amino]oxy]-2methylpropanoic acid, diphenylmethyl ester, monopotassium salt (2.5 g) was suspended in 5 ml of anisole and cooled to 0° C. Trifluoroacetic acid (12 ml) was slowly dropped in with stirring, maintaining the temperature at 0° C. After 3.5 hours, the solution was poured into 100 ml of ether, precipitating the desired product. The crude product was filtered off and purified by HP-20 chromatography using water/acetone (9:1) as eluent and yielding 620 mg of product, melting point 225°–230° C., dec.

EXAMPLE 3

[1-[[[[(Chloroacetyl)amino]sulfonyl]amino]carbonyl]-2-oxo-3-azetidinyl]carbamic acid, phenylmethyl ester (S)-3-[[(Phenylmethoxy)carbonyl]amino]-2-azetidinone (4.4 g) was suspended in 150 ml of dry ethyl acetate. The mixture was cooled to −50° C. and 3.3 g of chlorosulfonyl isocyanate was added with stirring; stirring was continued without cooling until the temperature reached 0° C. N-(Trimethylsilyl)chloroacetamide (6.0 g) was added and the solution was stirred overnight. The insoluble material was filtered off and the filtrate washed with water. The organic layer was extracted twice with saturated aqueous sodium bicarbonate. The alkaline aqueous layer was acidified to pH 1 with 20% hydrochloric acid and extracted twice with 150 ml portions of ethyl acetate. The organic layers were combined, dried and evaporated to dryness. The oily residue was dissolved in 50 ml of acetone and the pH was adjusted to 6.5 by addition of 1N potassium hydroxide. The solvent was removed in vacuo and the crystalline residue filtered with ether, yielding 3.9 g of the title compound.

EXAMPLE 4

[3S(R)]-N-[2-[[1-[[[(Acetylamino)sulfonyl]amino]carbonyl]-2-oxo-3-azetidinyl]amino]-2-oxo-1-phenylethyl]-4-ethyl-2,3-dioxo-1-piperazinecarboxamide, potassium salt Following the procedure of example 1B, but substituting (R)-α-[[(4-ethyl-2,3-dioxo-1-piperazinyl)carbonyl]amino]benzeneacetic acid for (Z)-2-amino-α-(methoxyimino)-4-thiazoleacetic acid, yielded the title compound melting point 160°–165° C., dec.

EXAMPLE 5

[3S(Z)]-2-Amino-N-1-[[[[(chloroacetyl)amino]sulfonyl]amino]carbonyl]-2-oxo-3-azetidinyl]-α-(methoxyimino)-4-thiazoleacetamide, potassium salt

[1-[[[[(Chloroacetyl)amino]sulfonyl]amino]carbonyl]-2-oxo-3-azetidinyl]carbamic acid, phenylmethyl ester (1.0 g; see example 3) was slowly added to 20 ml of 40% HBr in acetic acid at 10 °C. When the addition was complete the solution was stirred for 5 minutes. Dry diethyl ether (100 ml) was added and the precipitate was filtered off, washed with ether and dried carefully. This compound was dissolved in 50 ml of water, the pH adjusted to 6.5 with 1N KOH and the resulting solution freeze-dried. The compound obtained was dissolved in 50 ml of dry dimethylformamide and (Z)-2-amino-α-(methoxyimino)-4-thiazoleacetic acid, 0.04 g of N-hydroxybenzotriazole and 0.76 g dicyclohexylcarbodiimide are added and the solution was stirred overnight at ambient temperature. The precipitated urea was filtered off and the solvent removed in vacuo. The residue was chromatographed using HP-20 resin (eluent:water), yielding 0.19 g of product, melting point 215°–220° C.

EXAMPLE 6

[3S(Z)]-2-[[[1-(2-Amino-4-thiazolyl)-2-[[1[[[[(chloroacetyl)amino]sulfonyl]amino]carbonyl]-2oxo-3-azetidinyl]amino]-2-oxoethylidene]amino]oxy]-2-methylpropanoic acid, dipotassium salt

[1-[[[[(Chloroacetyl)amino]sulfonyl]amino]carbonyl]-2-oxo-3-azetidinyl]carbamic acid, phenylmethyl ester (2.0 g; see example 3) was added at 5° C. with stirring to 40 ml of 40% hydrogen bromide in acetic acid; after 5 minutes a clear solution was obtained. Dry ether (200 ml) was slowly dropped in and the precipitate was filtered off, washed with ether and dried carefully. The white powder was then dissolved in 50 ml of water and the pH adjusted to 6.5 and the solution freeze-dried. The compound obtained was dissolved in 100 ml of dry dimethylformamide and 2.72 g of (Z)-2-amino-α-[[2-(diphenylmethoxy)-1,1-dimethyl-2-oxoethoxy]imino]-4-thiazoleacetic acid, 0.08 g N-hydroxybenzotriazole and 1.52 g of dicyclohexylcarbodiimide was added and the solution was stirred for 12 hours. The precipitate was filtered off and the solvent removed in vacuo. The residue was stirred with 100 ml of dry ether and filtered. The compound was then suspended in 6 ml of anisole and cooled to −15° C. At this point 12 ml of trifluoroacetic acid was dropped in with stirring at such a rate, that the temperature did not exceed −10° C. After completion of the addition, stirring was continued at −10° C. for 2 hours. Cold ether (200 ml) was added and the precipitated compound was filtered off, washed with ether, dried and dissolved in 50 ml of acetone/water (1:1). The pH was adjusted to 6.5 with 1N KOH, the acetone removed in vacuo and the remaining aqueous solution freeze-dried; 2.25 g of crude title compound was obtained. Purification was achieved by HP-20 chromatography (water eluent), yielding 0.5 g of product, melting point 220°–225° C., dec.

EXAMPLE 7

[3S(Z)]-2-[[[1-(2-Amino-4-thiazolyl)-2-[[1[[[[(methoxyacetyl)amino]sulfonyl]amino]carbonyl]-2-oxo-3-azetidinyl]amino]-2-oxoethylidene]amino]oxy]-2-methylpropanoic acid, dipotassium salt (S)-[1-[[[[(Methoxyacetyl)amino]sulfonyl]amino]carbonyl]-2-oxo-3-azetidinyl]carbamic acid, phenylmethyl ester, monopotassium salt (S)-3-[[(Phenylmethoxy)carbonyl]amino]-2-azetidinone (4.4 g) was suspended in 100 ml of dry ethyl acetate. The mixture was cooled to −30° C. and 3.12 g of chlorosulfonylisocyanate was added with stirring. The cooling was stopped and when the temperature had reached 0° C. a clear solution was obtained. After 30 minutes at 0° C. 13.9 g of N-trimethylsilyl methoxyacetamide were added and stirring was continued for 24 hours at ambient temperature. After this time the ethyl acetate solution was washed with water, dried and the solvent removed. The residue was dissolved in acetone/water (9:1) and the pH was adjusted to 6.5 with 1N KOH. The acetone was removed in vacuo and the aqueous solution was freeze-dried.

(B)

[3S(Z)]-2-[[[1-(2-Amino-4-thiazolyl)-2-[[1-[[[[(methoxyacetyl)amino]sulfonyl]amino]carbonyl]-2-oxo-3-azetidinyl]amino]-2-oxo-ethylidene]amino]oxy]-2-methylpropanoic acid, dipotassium salt (S)-[1-[[[[(Methoxyacetyl)amino]sulfonyl]amino]carbonyl]-2-oxo-3-azetidinyl]carbamic acid, phenylmethyl ester, monopotassium salt (0.43 g) was dissolved in 50 ml of dry dimethylformamide. Palladium on charcoal (10%; 0.25 g) was added and hydrogen was bubbled through for 30 minutes with stirring. The catalyst was filtered off and 0.42 g of (Z)-2-amino-α-[[2-(diphenylmethoxy)-1,1-dimethyl-2-oxoethoxy]imino]-4-thiazoleacetic acid, 0.01 g N-hydroxybenzotriazole and 0.24 g of dicyclohexylcarbodiimide was added; the solution was stirred at ambient temperature for 12 hours. The precipitate was filtered off and the solvent removed in vacuo. The residue was suspended in diethyl ether and the precipitate filtered off (0.76 g). This compound was suspended in 3 ml of anisole and cooled to −15° C.; 6 ml of trifluoroacetic acid was slowly dropped in with stirring, so that the temperature did not exceed −10° C. After the addition was complete, the temperature was maintained for 2 hours. Cold diethyl ether (100 ml) was added and the precipitate was filtered off, dried and dissolved in water. The pH was adjusted to 6.5 by addition of 1N KOH and the solution was chromatographed on HP-20 resin, using water as eluent, yielding 200 mg of product, melting point 245°–250° C., dec.

EXAMPLE 8

[3S(Z)]-2-Amino-N-[1-[[[[(methoxyacetyl)amino]-sulfonyl]amino]carbonyl]-2-oxo-3-azetidinyl]-α-(methoxyimino)-4-thiazoleacetamide, potassium salt (S)-[1-[[[[(Methoxyacetyl)amino]sulfonyl]amino]carbonyl]-2-oxo-3-azetidinyl]carbamic acid, phenylmethyl ester, monopotassium salt (0.5 g; see example 7A) was hydrogenated in 30 ml of dry dimethylformamide in the presence of 0.25 g 10% palladium on charcoal for 30 minutes. The catalyst was filtered off and 0.22 g of (Z)-2-amino-α-(methoxyimino)-4-thiazoleacetic acid, 0.01 g of N-hydroxybenzotriazole and 0.21 g of dicyclohexylcarbodiimide were added. The solution was stirred overnight, filtered and evaporated to dryness. The residue was chromatographed (HP-20, water as eluent), yielding 0.12 g of product, melting point 170°–175° C.,dec.

EXAMPLE 9

[3S(Z)-2-[[[1-(2-Amino-4-thiazolyl)-2-[[1-[[[benzoylamino)sulfonyl]amino]carbonyl]-2-oxo-3-azetidinyl]amino]-2-oxoethylidene]amino]-oxo]-2-methylpropanoic acid, dipotassium salt (A)
(S)-[1-[[(Aminosulfonyl)amino]carbonyl]-2-oxo-3-azetidinyl]carbamic acid, phenylmethyl ester, potassium salt

Method I (S)-(2-Oxo-3-azetidinyl)carbamic acid, phenylmethyl ester (11 g) was dissolved in a mixture of 200 ml of acetonitrile and 50 ml of dichloromethane. The mixture was cooled to −50° C. and a solution of chlorosulfonyl isocyanate (9 g) in 25 ml of dichloromethane was added with stirring. After warming the mixture to −30° C. a solution of 6 g of ammonia in 60 ml of acetonitrile was added slowly. The reaction temperature was raised to −10° C. and finally to 0°–5° C. The reaction time was 3 hours. The ammonium salt of the title compound precipitated and was filtered by suction (20 g). The crude product was purified by HP-20 chromatography (100–200 mesh) eluting with 2000 ml of water and water/acetone (8:2); 20 ml fractions were taken. The elution was monitored by thin-layer chromatography. From fractions 142–154, 9.3 g of product was obtained by evaporation.

The ammonium salt of the title compound was dissolved in 100 ml of water, layered with 200 ml of ethyl acetate and acidified. After separation and washing of the aqueous layer twice with ethyl acetate, the organic layer was washed with saturated sodium chloride solution, dried with anhydrous magnesium sulfate and evaporated to yield 8.1 g of the free acid of the title compound.

Method II

A mixture of (S)-(2-oxo-3-azetidinyl)carbamic acid, phenylmethyl ester (11 g) in 175 ml of dichloromethane was cooled to −30° C. While stirring, 7.7 g of chlorosulfonyl isocyanate in 75 ml dichloromethane was added dropwise within 15 minutes. The temperature of the solution was allowed to rise to 0° C. over 30 minutes. Subsequently the clear solution was again cooled to −30° C. and 8.8 g of bis-(trimethylsilyl)amine dissolved in 30 ml of dichloromethane, was dropped in, while passing dry nitrogen through the flask. After an hour the reaction temperature was allowed to rise to −15° C. and was maintained for an additional 30 minutes. The solvent was distilled off in vacuo, and the residue was triturated with 400 ml of ether to give a solid (16.6 g) which was washed with an additional 20 ml of ether. From the ethereal mother liquor there was obtained a second crop of 4.2 g of product.

The crude material (18.0 g) along with about 20 g of HP-20 resin was suspended in 30 ml of water and the mixture was chromatographed on an HP-20 column eluted with (a) 3 L of water; (b) 2.5 L of water/acetone (8:2); (3) 4 L of water/acetone (7:3); (d) 6 L of water-/acetone (6:4). Fraction d yielded 6.2 g of the title compound, melting point 150°–152° C.

(B)
(S)-[1-[[[(Benzoylamino)sulfonyl]amino]carbonyl]-2-oxo-3-azetidinyl]carbamic acid, phenylmethyl ester, potassium salt (S)-[1-[[(Aminosulfonyl)amino]carbonyl]-2-oxo-3-azetidinyl]carbamic acid, phenylmethyl ester, potassium salt (2.3 g) and 2.2 g of potassium carbonate were stirred in 50 ml of dry dimethylformamide with 5 g of benzoyl chloride and 0.6 g of dimethylaminopyridine overnight. The solvent was removed in vacuo and the residue was extracted at pH 1 (aqueous solution) with ethyl acetate. The organic layer was dried and evaporated to dryness. The residue was dissolved in water-/acetone (1:9) and the pH adjusted to 6.5 with 1N KOH. The acetone was removed in vacuo and the remaining aqueous solution freeze-dried. Purification of the resulting white powder was achieved by HP-20 chromatography using water/acetone (9:1) as eluent, and yielding 1.1 g of product melting point 96°–99° C., dec.

(C)
[3S(Z)]-2-[[[1-[2-Amino-4-thiazolyl)-2[[1-[[[(benzoylamino)sulfonyl]amino]carbonyl]-2-oxo-3-azetidinyl]amino]-2-oxoethylidene]amino]-oxy]-2-methylpropanoic acid, dipotassium salt (S)-[1-[[[(Benzoylamino)sulfonyl]amino]carbonyl]-2-oxo-3-azetidinyl]carbamic acid, phenylmethyl ester, potassium salt (0.5 g) was hydrogenated in 100 ml of dry dimethylformamide in the presence of 0.25 g of 10% palladium on charcoal for 1 hour. The catalyst was filtered off and 0.46 g of (Z)-2-amino-α-[[2-(diphenylmethoxy)-1,1-dimethyl-2-oxoethoxy]imino]-4-thiazoleacetic acid, 0.01 g N-hydroxybenzotriazole and 0.24 g of dicyclohexylcarbodiimide were added and the solution was stirred for 12 hours. The solvent was distilled off in vacuo and the residue was filtered off with 100 ml of ether and dried (0.92 g). This compound was suspended in 2 ml of anisole, cooled to −10° C. and 4 ml trifluoroacetic acid was added with stirring. The temperature was maintained for 5 hours. After this time 100 ml of dry ether was added and the precipitated compound was filtered off, dissolved in 5 ml of water and the pH was adjusted to 6.5 with 1N KOH. The resulting aqueous solution was chromatographed on HP-20 resin (eluting with water) and yielded 0.24 g of product, melting point 225°–230° C., dec.

EXAMPLE 10

[3S(R)]-N-[2-][[[[(Benzoylamino)sulfonyl]amino]carbonyl]-2-oxo-3-azetidinyl]amino]-2-oxo-1-phenylethyl]-4-ethyl-2,3-dioxo-1-piperazine carboxamide, potassium salt (S)-[1-[[[(Benzoylamino)sulfonyl]amino]carbonyl]-2-oxo-3-azetidinyl]carbamic acid, phenylmethyl ester, potassium salt (0.25 g; see example 9B) was hydrogenated as described in example 9C. (R)-α-[[(4-Ethyl-2,3-dioxo-1-piperazinyl)carbonyl]amino]benzeneacetic acid (0.17 g), 0.01 g of N-hydroxybenzotriazole and 0.13 g of dicyclohexylcarbodiimide were added to the resulting solution which was stirred overnight. The solvent was distilled off in vacuo and the residue chromatographed using HP-20 resin and water/acetone (19:1) as eluent, yielding 0.14 g of product, melting point 180°–185° C., dec.

EXAMPLE 11

[3S(Z)]-2-Amino-N-[1-[[[(benzoylamino)sulfonyl]amino]carbonyl]-2-oxo-3-azetidinyl]-α-(methoxyimino)-4-thiazoleaoetamide, potassium salt (S)-[1-[[[(Benzoylamino)sulfonyl]amino]carbonyl]-2-oxo-3-azetidinyl]carbamic acid, phenylmethyl ester, potassium salt (0.25 g; see example 9B) was hydrogenated as described in example 9C. To the resulting solution 0.01 g of N-hydroxybenzotriazole, 0.11 g of (Z)-2-amino-α-(methoxyimino)-4-thiazoleacetic acid and 0.13 g of dicyclohexylcarbodiimide were added. After stirring overnight at room temperature, the solvent was removed in vacuo and the residue chromatographed using HP-20 resin and water/acetone (19:1) as eluent, yielding 0.05 g of product, melting point 205°–210° C.

EXAMPLE 12

(S)-[1-[[[[(Acetyl)methylamino]sulfonyl]amino]carbonyl]-2-oxo-3-azetidinyl]carbamic acid, phenylmethyl ester (S)-3-[[(Phenylmethoxy)carbonyl]amino]-2-azetidinone (2.2 g) was suspended in 100 ml of anhydrous tetrahydrofuran and cooled to −50° C. with stirring. Chlorosulfonylisocyanate (1.56 g) was added and the temperature was maintained at 0° C. for 30 minutes. After this time 3.51 g of heptamethyl disilazane was added and stirring at room temperature was continued overnight. Acetyl chloride (3.14 g) was added and the solution was stirred for an additional 48 hours. The solvent was removed in vacuo, and the residue dissolved in ethyl acetate and extracted twice with 50 ml portions of water. The aqueous layer was discarded and the ethyl acetate solution was dried with Na₂SO₄ and evaporated to dryness. The residue was dissolved in acetone/water (9:1), the pH adjusted to 6.5 with 1N KOH and the acetone removed in vacuo. The remaining aqueous solution was freeze-dried. The resulting crude compound (1.9 g) was purified by HP-20 chromatography, yielding 1.03 g of product.

EXAMPLE 13

[3S(Z)]-2-Amino-N-[1-[[[[(2-methylpropanoyl)amino]sulfonyl]amino]carbonyl]-2-oxo-3-azetidinyl]-α-(methoxyimino)-4-thiazoleacetamide potassium salt (S)-3-[[(Phenylmethoxy)carbonyl]amino]-2-azetidinone (2.2 g) was suspended in 100 ml of dry ethyl acetate, cooled to −50° C. and 1.56 g chlorosulfonylisocyanate was added. After 30 minutes at 0° C. a clear solution was obtained and 4.78 g of N-trimethylsilyl 2-methylpropionamide was added and stirring at ambient temperature was continued for 12 hours. The solution was washed with 100 ml of water, dried and evaporated to dryness. The residue was dissolved in water/acetone (1:9) and the pH adjusted to 6.5 with 1N KOH. Acetone was removed in vacuo and the remaining aqueous solution freeze-dried, yielding 0.28 g of compound. This compound was dissolved in 20 ml of dry dimethylformamide and hydrogenated with 0.1 g of 10% palladium on charcoal for 30 minutes. The catalyst was filtered off and 0.1 g of (Z)-2-amino-α-(methoxyimino)-4-thiazoleacetic acid, 0.01 g of N-hydroxybenzotriazole and 0.13 g of dicyclohexylcarbodiimide were added and the mixture was stirred overnight at room temperature. The solvent was removed in vacuo and the residue chromatographed on HP-20 resin eluting with H₂O/acetone (19:1) and yielding 50 mg of product, melting point 185°–190° C., dec.

EXAMPLE 14

[3S(Z)]-2Amino-N-[1-[[[[(aminocarbonyl)amino]sulfonyl]amino]carbonyl]-2-oxo-3-azetidinyl]-α-(methoxyimino)-4-thiazoleacetamide, potassium salt (A)

(S)-[1-[[[[(Aminocarbonyl)amino]sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (13.2 g) was suspended in 300 ml of dry tetrahydrofuran at 0° C. Chlorosulfonylisocyanate (11.1 g) dissolved in 80 ml of dry dichloromethane was dropped in with stirring. The temperature was maintained with cooling at 0° C. for 30 minutes. Trimethylsilyl urea (10.5 g) was added and stirring was continued at room temperature overnight. The solvent was removed in vacuo and 200 ml of methanol was added. The solution was stirred for 30 minutes, the solvent evaporated and the residue treated with 200 ml of ethyl acetate and 100 ml of water. The organic layer was separated, dried and filtered. After removal of the solvent, the oily residue was dissolved in 100 ml of acetone and 10 ml of water, and the pH was adjusted to 6.5 by addition of 1N potassium hydroxide. After evaporation of the solvent, the title compound remained. Yield 11.0 g; melting point 120°–125° C., dec.

(B)

[3S(Z)]-2-Amino-N-[1-[[[[(aminocarbonyl)amino]sulfonyl]amino]carbonyl]-2--oxo-3-azetidinyl]-α-(methoxyimino)-4-thiazoleacetamide, potassium salt (S)-[1-[[[[(Aminocarbonyl)amino]sulfonyl]amino]carbonyl]-2-oxo-3-azetidinyl]carbamic acid, phenylmethyl ester, potassium salt (1.4 g) was hydrogenated in 100 ml of dry dimethylformamide with 0.7 g of 10% palladium on charcoal as a catalyst. After 30 minutes the hydrogenation was completed, the catalyst filtered off and 0.66 g of (Z)-2-amino-α-(methoxyimino)-4-thiazoleacetic acid and 0.2 g of N-hydroxybenzotriazole were added. Dicyclohexylcarbodiimide (720 mg), dissolved in 100 ml of dry dimethylformamide was slowly dropped in with stirring during a period of 10 hours. Stirring was continued for an additional 12 hours. The mixture was cooled to 0° C., the precipitated urea filtered off, the solvent removed in vacuo and the residue chromatographed on HP-20 resin using water as eluent. Yield 900 mg; melting point 205°–210° C., dec.

EXAMPLE 15

[3S(Z)]-2-[[[2-[[1-[[[[(Aminocarbonyl)amino]sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt (S)-[1-[[[[(Aminocarbonyl)amino]sulfonyl]amino]carbonyl]-2-oxo-3-azetidinyl]carbamic acid, phenylmethyl ester, potassium salt (1.98 g; see example 14A) was hydrogenated in the presence of 1 g of 10% palladium on charcoal in 200 ml of dry dimethylformamide for 30 minutes. The catalyst was filtered off and 300 mg of N-hydroxybenzotriazole and 2.5 g of (Z)-2-amino-α-[[2-(diphenylmethoxy)-1,1-dimethyl-2-oxoethoxy]imino]-4-thiazoleacetic acid was added. Dicyclohexylcarbodiimide (1.1 g), dissolved in 100 ml of dimethylformamide was slowly dropped in (10 hours). When the addition is complete, stirring was continued for an additional 10 hours. The solvent was removed in vacuo and the solid residue was suspended in 10 ml of anisole and cooled to 0° C. At this temperature 20 ml of trifluoroacetic acid was dropped in with stirring. The temperature was maintained at 0° C. with cooling. After 3.5 hours, the reaction was complete and the solution was poured into 200 ml of ether. The precipitate was filtered off, dried and dissolved in 10 ml of water/acetone (1:1), and the pH was adjusted to 6.5 by the addition of 1 N potassium hydroxide. The acetone was removed in vacuo and the aqueous phase chromatographed on HP-20 resin using water as eluent. Yield 1.5 g; melting point 258° C., dec.

EXAMPLE 16

[3S(R)]-N-[2-[[1-[[[[(Aminocarbonyl)amino]sulfonyl]amino]carbonyl]-2-oxo-3-azetidinyl]amino]-2-oxo-1-phenylethyl]-4-ethyl-2,3-dioxo-1-piperazinecarboxamide, potassium salt (S)-[1-[[[[(Aminocarbonyl)amino]sulfonyl]amino]carbonyl]-2-oxo-3-azetidinyl]carbamic acid, phenylmethyl ester, potassium salt (1.34 g; see example 14A) was hydrogenated with 0.6 g of 10% palladium on charcoal as catalyst in 100 ml of dry dimethylformamide for 30 minutes. The catalyst was filtered off and 1.23 g of (R)-α-[[(4-ethyl-2,3-dioxo-1-piperazinyl)carbonyl]amino]benzeneacetic acid and 100 mg of N-hydroxybenzotriazole were added. Dicyclohexylcarbodiimide (0.8 g), in 100 ml of dimethylformamide was dropped in with stirring over a period of 10 hours. Stirring was continued for an additional 10 hours. The solvent was removed in vacuo and the residue chromatographed on HP-20 resin, using water as eluent. Yield 590 mg; melting point 198° C., dec.

EXAMPLE 17

[3S(Z)]-2-Amino-α-(methoxyimino)-N-[1-[[[[(methylamino)carbonyl]amino]sulfonyl]amino]carbonyl]-2-oxo-3-azetidinyl]-4-thiazoleacetamide, potassium salt (A)

(S)-[1-[[[[(Methylamino)carbonyl]amino]sulfonyl]amino]carbonyl]-2-oxo-3-azetidinyl]carbamic acid, phenylmethyl ester, potassium salt (S)-[1-[[(Aminosulfonyl)amino]carbonyl]-2-oxo-3-azetidinyl]carbamic acid, phenylmethyl ester, potassium salt (1 g; see example 9A) was dissolved in 20 ml of dry dimethylformamide. Methylisocyanate (500 mg), was added and the solution was stirred overnight at ambient temperature. The solvent was removed in vacuo and the residue was treated with acetone/ether (1:1) and filtered. Yield 0.9 g; melting point 153°–160° C., dec.

(B)

[3S(Z)]-2-Amino-α-(methoxyimino)-N-[1-[[[[(methylamino)carbonyl]amino]sulfonyl]amino]carbonyl]-2-oxo-3-azetidinyl]-4-thiazoleacetamide, potassium salt (S)-[1-[[[[(Methylamino)carbonyl]amino]sulfonyl]amino]carbonyl]-2-oxo-3-azetidinyl]carbamic acid, phenylmethyl ester, potassium salt (437 mg) was hydrogenated in 50 ml of dry dimethylformamide in the presence of 200 mg of 10% palladium on charcoal. After 45 minutes the reaction was complete and the catalyst was filtered off. (S)-2-Amino-α-(methoxyamino)-4-thiazoleacetic acid (220 mg), 50 mg of N-hydroxybenzotriazole and 300 mg of dicyclohexylcarbodiimide were added with stirring at ambient temperature. Stirring was continued for 12 hours, the solution cooled to 0° C. and the precipitated urea was filtered off. The solvent of the mother liquor was removed in vacuo and the residue was chromatographed on HP-20 resin, using water. Yield 305 mg; melting point 220°–225° C., dec.

EXAMPLE 18

[3S(R)]-4-Ethyl-N-[2-[[1-[[[[methyl[methylamino)-carbonyl]amino]sulfonyl]amino]carbonyl]-2-oxo-3-azetidinyl]amino]-2-oxo-1-phenylethyl]-2,3-dioxo-1-piperazinecarboxamide, potassium salt (A)

(S)-[1-[[[[Methyl[(methylamino)carbonyl]amino]sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (4.4 g) was suspended in 100 ml of dry tetrahydrofuran and the mixture was cooled to −10° C. At this temperature, 1.6 g of chlorosulfonylisocyanate was added and the reaction mixture was allowed to reach room temperature. Trimethylsilyl-N,N'-dimethylurea (5.2 g) were added and stirring at ambient temperature was continued for 12 hours. The solvent was removed in vacuo and the residue was dissolved in 100 ml of ethyl acetate. The organic solution was washed twice with 50 ml portions of water, with 50 ml of 2 N phosphoric acid and with brine. The organic layer was evaporated to dryness, the residue dissolved in water/acetone (1:1) (50 ml). The pH was adjusted to 6.5 with 1N potassium hydroxide. The acetone was removed in vacuo and the aqueous solution freeze dried to yield 8 g of crude title compound pure enough for further reactions.

(B)

[3S(R)]-4-Ethyl-N-[2-[[1-[[[[methyl[(methylamino)carbonyl]amino]sulfonyl]amino]carbonyl]-2-oxo-3-azetidinyl]amino]-2-oxo-1-phenylethyl]-2,3-dioxo-1-piperazinecarboxamide, potassium salt (S)-[1-[[[[Methyl[(methylamino)carbonyl]amino]sulfonyl]amino]carbonyl]-2-oxo-3-azetidinyl]carbamic acid, phenylmethyl ester, potassium salt (900 mg) was hydrogenated in 50 ml of dry dimethylformamide in the presence of 400 mg of 10% palladium on charcoal. The hydrogen uptake ceased after about 30 minutes. The catalyst was filtered off and 700 mg (R)-α-[[(4-ethyl-2,3-dioxo-1-piperazinyl)carbonyl]amino]benzeneacetic acid, 100 mg of N-hydroxybenzotriazole and 600 mg of dicyclohexylcarbodiimide were added with stirring. After 12 hours at ambient temperature, the precipitated urea was filtered off, and the solvent removed in vacuo. The residue was chromatographed on HP-20 resin, using water/acetone (9:1) as eluent. Yield 700 mg; melting point 177° C., dec.

EXAMPLE 19

[3S(Z)]-2-[[[1-(2-Amino-4-thiazolyl)-2-[[1-[[[[methyl[(methylamino)carbonyl]amino]sulfonyl]amino]carbonyl]-2-oxo-3-azetidinyl]amino]-2-oxoethylidene]amino]oxy]-2-methylpropanoic acid, dipotassium salt (S)-[1-[[[[Methyl[(methylamino)carbonyl]amino]sulfonyl]amino]carbonyl]-2-oxo-3-azetidinyl]carbamic acid, phenylmethyl ester, potassium salt (900 mg; see example 18A) was hydrogenated in 50 ml of dry dimethylformamide in the presence of 450 mg of 10% palladium on charcoal for 30 minutes. The catalyst was filtered off and 1 g of (Z)-2-amino-α-[[2-(diphenylmethoxy)-1,1-dimethyl-2-oxoethoxy]imino]-4-thiazoleacetic acid, 100 mg of N-hydroxybenzotriazole and 600 mg of dicyclohexylcarbodiimide were added with stirring at ambient temperature. After 12 hours, the solution was cooled to 0° C. and the precipitated urea was filtered off. The solution was evaporated to dryness and the residue was filtered off with 50 ml of ethyl acetate. The crude compound was suspended in 2 ml of anisole, cooled to −5° C. and 6 ml of trifluoroacetic acid was dropped in at such a rate that the temperature could be maintained at 0° C. After 2 hours, 100 ml of dry ether was added and the precipitate was filtered off, washed with ether and dried. The crude compound was dissolved in 20 ml of water and the pH adjusted to 6.5 with 1N potassium hydroxide. After freeze drying, the crude potassium salt was chromatographed using HP-20 resin and water as eluent and then freeze-dried. Yield 400 mg; melting point 220° C., dec.

EXAMPLE 20

[3S(Z)]-2-Amino-α-(methoxyimino)-N-[1-[[[[methyl[(methylamino)carbonyl]amino]sulfonyl]amino]carbonyl]-2-oxo-3-azetidinyl]-4-thiazoleacetamide, potassium salt (S)-[1-[[[[Methyl[(methylamino)carbonyl]amino]sulfonyl]amino]carbonyl]-2-oxo-3-azetidinyl]carbamic acid, phenylmethyl ester, potassium salt (440 mg; see example 18A) was hydrogenated as described in example 6. (Z)-2-Amino-α-(methoxyimino)-4-thiazoleacetic acid (220 mg), 50 mg of N-hydroxybenzotriazole and 250 ml of dicyclohexylcarbodiimide were added after removal of the catalyst. Stirring at ambient temperature was continued for 12 hours. The solvent was removed in vacuo and the residue chromatographed on HP-20 resin, using water/acetone (9:1) as eluent. Yield 350 mg (isolated by freeze drying); melting point 192° C., dec.

EXAMPLE 21

[3S(Z)]-2-[[[1-(2-Amino-4-thiazolyl)-2-[[1-[[[[(dimethylamino)carbonyl]amino]sulfonyl]amino]carbonyl]-2-oxo-3-azetidinyl]amino]-2-oxoethylidene]amino]oxy]-2-methylpropanoic acid, potassium salt (A)

(S)-[1-[[[[(Dimethylamino)carbonyl]amino]sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (4.4 g) was suspended in 150 ml of ethyl acetate and cooled to −15° C. Chlorosulfonylisocyanate (3.0 g) was added and the mixture was stirred at 0° C. until a clear solution was obtained. N,N-Dimethylurea (2 g) and 2 g of triethylamine were added and stirring was continued overnight. The precipitate was filtered off and the mother liquor washed with two 50 ml portions of water, 50 ml of 2N phosphoric acid and brine. The solvent was removed in vacuo and the residue was dissolved in 50 ml of water/acetone (1:1). The pH was adjusted to 6.5 with 1N potassium hydroxide. The acetone was removed in vacuo and the aqueous solution was freeze dried. Crude title compound (7 g) was obtained, which was pure enough for further manipulation.

(B)

[3S(Z)]-2-[[[1-[2-Amino-4-thiazolyl)-2-[[1-[[[[(dimethylamino)carbonyl]amino]sulfonyl]amino]carbonyl]-2-oxo-3-azetidinyl]amino]-2-oxoethylidene]amino]oxy]-2-methylpropanoic acid, potassium salt (S)-[1-[[[[(Dimethylamino)carbonyl]amino]sulfonyl]amino]carbonyl]-2-oxo-3-azetidinyl]carbamic acid, phenylmethyl ester, potassium salt (451 mg) was dissolved in 50 ml of anhydrous dimethylformamide, 200 ml of 10% palladium on charcoal was added and hydrogen was bubbled through the solution for 45 minutes. The catalyst was filtered off and 450 mg of (Z)-2-amino-α-[[2-(diphenylmethoxy)-1,1-dimethyl-2-oxoethoxy]imino]-4-thiazoleacetic acid, 100 mg of N-hydroxybenzotriazole and 300 mg of dicyclohexylcarbodiimide were added and the solution was stirred at ambient temperature for 12 hours. The precipitated urea was filtered off and the solvent removed in vacuo. The residue was chromatographed using HP-20 resin and water/acetone (7:3) as eluent. The benzhydryl ester of the title compound (600 mg) was isolated by freeze drying. This compound was suspended in 2 ml of anisole, the mixture cooled to −10° C. and 4 ml of trifluoroacetic acid was slowly dropped in, so that the temperature did not exceed −5° C. When the addition was complete, stirring at −5° C. was continued for 2 to 5 hours. The title compound was precipitated by the addition of 100 ml of ether, filtered off, dissolved in 5 ml of water and the pH adjusted to 6.5 with 2N potassium hydroxide. The solution was chromatographed on HP-20 resin using water as eluent. Yield 280 mg; melting point 191° C., dec.

EXAMPLE 22

[3S(Z)]-2-[[[1-(2-Amino-4-thiazolyl)-2-[[1-[[[[(3-ethyl-2-oxo-1-imidazolidinyl)carbonyl]amino]sulfonyl]amino]carbonyl]-2-oxo-3-azetidinyl]amino]-2-oxoethylidene]amino]oxy]-2-methylpropanoic acid, dipotassium salt (A)

(S)-[1-[[[[(3-Ethyl-2-oxo-1-imidazolidinyl)carbonyl]amino]sulfonyl]amino]carbonyl]-2-oxo-3-azetidinyl]-carbamic acid, phenylmethyl ester, potassium salt (S)-3-[[(Phenylmethoxy)carbonyl]amino]-2azetidinone (6.6 g) was suspended in 200 ml of anhydrous ethyl acetate and the mixture was cooled to −15° C. At this temperature, 5 g of chlorosulfonylisocyanate was added with stirring at 0° C. until a clear solution was obtained (10 minutes). Triethylamine (4 g) and 5.2 g of 1-aminocarbonyl-3-ethylimidazolidin-2-one were added and stirring was continued at room temperature for 12 hours. The reaction mixture was washed with two 50 ml portions of water, 50 ml of 2 N phosphoric acid and brine. The organic phase was evaporated to dryness, the residue dissolved in 150 ml of water/acetone (1:1) and the pH was adjusted to 6.5 with 1 N potassium hydroxide. The acetone was distilled off in vacuo and the remaining aqueous solution was freeze dried. The crude title compound (12.2 g) was pure enough for further reactions.

(B)

[3S(Z)]-2-[[[1-(2-Amino-4-thiazolyl)-2-[[1-[[[[(3-ethyl-2-oxo-1-imidazolidinyl)carbonyl]amino]sulfonyl]amino]carbonyl]-2-oxo-3-azetidinyl]amino]-2-oxoethylidene]amino]oxy]-2-methylpropanoic acid, dipotassium salt (S)-[1-[[[[(3-Ethyl-2-oxo-1-imidazolidinyl)carbonyl]amino]sulfonyl]amino]carbonyl]-2-oxo-3-azetidinyl]-carbamic acid, phenylmethyl ester, potassium salt (520 mg) was hydrogenated in 50 ml of anhydrous dimethylformamide in the presence of 200 mg of 10% palladium on charcoal for 40 minutes. The catalyst was filtered off, 460 mg of (Z)-2-amino-α-[[2-(diphenylmethoxy)-1,1-dimethyl-2-oxoethoxy]imino]-4-thiazoleacetic acid, 100 ml of N-hydroxybenzotriazole and 300 mg of dicyclohexylcarbodiimide were added and the solution was stirred overnight. The solvent was distilled off in vacuo and the residue was filtered off with ethyl acetate, suspended in 2 ml of anisole and cooled to −10° C. Trifluoroacetic acid (4 ml) were dropped in at such a rate that the temperature did not exceed −5° C. Stirring at this temperature was continued for 2 hours. After addition of 100 ml ether, the precipitate was filtered off, dissolved in 10 ml of water, the pH adjusted to 6.5 with 1 N potassium hydroxide and the aqueous solution was chromatographed on HP-20 using water as eluent, and the title compound isolated by freeze drying. Yield 250 mg; melting point 245° C., dec.

EXAMPLE 23

[3S(Z)]-2-Amino-α-(ethoxyimino)-[1-[[[[(3-ethyl-2-oxo-1-imidazolidinyl)carbonyl]a-mino]sulfonyl]amino]-carbonyl]-2-oxo-3-azetidinyl]-4-thiazoleacetamide, potassium salt (S)-[1-[[[[(3-Ethyl-2-oxo-1-imidazolidinyl)carbonyl]amino]sulfonyl]amino]carbonyl]-2-oxo-3-azetidinyl]-carbamic acid, phenylmethyl ester, potassium salt (520 mg; see example 22A) was hydrogenated in 50 ml of dimethylformamide in the presence of 200 mg of 10% palladium on charcoal for 40 minutes. The catalyst was filtered off and 230 mg of (Z)-2-amino-α-(ethoxyimino)-4-thiazoleacetic acid, 100 mg of N-hydroxybenzotriazole and 300 mg of dicyclohexylcarbodiimide were added. The solution was agitated at room temperature for 12 hours. After this time the solvent was removed in vacuo and the residue filtered with ethyl acetate. Purification of the crude compound was accomplished by HP-20 chromatography using water/acetone (9:1) as eluent, and the title compound isolated by freeze drying. Yield 420 mg; melting point 125° C.

EXAMPLE 24

[3S(Z)]-2-Amino-N-[1-[[[[(3-ethyl-2-oxo-1-imidazolidinyl)carbonyl]amino]sulfonyl]amino]carbonyl]-2-oxo-3-azetidinyl]-α-(methoxyimino)-4-thiazoleacetamide, potassium salt Following the procedure of example 23, but replacing (Z)-2-amino-α-(ethoxyimino)-4-thiazoleacetic acid by (Z)-2-amino-α-(methoxyimino)-4-thiazoleacetic acid, yielded 400 mg of the title compound; melting point 176° C., dec.

EXAMPLE 25

[3S(R)]-4-Ethyl-N-[2-[[1-[[[[(3-ethyl-2-oxo-1-imidazolidinyl)carbonyl]amino]sulfonyl]amino]carbonyl]-2-oxo-3-azetidinyl]amino]-2-oxo-1-phenylethyl]-2,3-dioxo-1-piperazinecarboxamide, potassium salt (S)-1-[[[[(3-Ethyl-2-oxo-1-imidazolidinyl)carbonyl]amino]sulfonyl]amino]carbonyl]-2-oxo-3-azetidinyl]-carbamic acid, phenylmethyl ester, potassium salt (520 mg; see example 22A) was hydrogenated in 50 ml of dimethylformamide in the presence of 200 mg of 10% palladium on charcoal for 40 minutes. After filtration, 330 mg of (R)-α-[[(4-ethyl-2,3-dioxo-1-piperazinyl)carbonyl]amino]benzeneacetic acid, 300 mg of dicyclohexylcarbodiimide and 100 mg of N-hydroxybenzotriazole were added and the solution was stirred for 12 hours at room temperature. The solution was evaporated in vacuo to dryness and the residue filtered with ethyl acetate.

Purification of the crude compound was achieved by chromatography on HP-20 resin using water/acetone (9:1) as eluent. Yield 480 mg; melting point 181° C., dec.

EXAMPLE 26

[3S(Z)]-2-Amino-α-(methoxyimino)-N-[1-[[[[(4-ethyl-2,3-dioxo-1-piperazinyl)carbonyl]amino]sulfonyl]amino]carbonyl]-2-oxo-3-azetidinyl]-4-thiazoleacetamide, potassium salt (A)

(S)-[1-[[[[(4-Ethyl-2,3-dioxo-1-piperazinyl)carbonyl]amino]sulfonyl]amino]carbonyl]-2-oxo-3-azetidinyl]-carbamic acid, phenylmethyl ester, potassium salt (S)-3-[[(Phenylmethoxy)carbonyl]amino]-2-azetidinone (4.4 g) was suspended in 200 ml of ethyl acetate and at −15° C., 3 g of chlorosulfonylisocyanate was added with stirring. After 15 minutes at 0° C. a clear solution was obtained. 2.5 g Triethylamine and 4 g of 1-aminocarbonyl-4-ethyl-2,3-dioxopiperazine was added and stirring was continued for 16 hours. The mixture was washed with two 50 ml portions of water, 50 ml of 2 N phosphoric acid and brine. After evaporation of the solvent, the residue was dissolved in 100 ml of acetone/water (1:1), the pH adjusted to 6.5, the acetone removed and 8 g of crude compound isolated by freeze drying.

(B)

[3S(Z)]-2-Amino-α-(methoxyimino)-N-[1-[[[[[(4-ethyl-2,3-dioxo-1-piperazinyl)carbonyl]amino]sulfonyl]amino]carbonyl]-2-oxo-3-azetidinyl]-4-thiazoleacetamide, potassium salt (S)-[1-[[[[[(4-Ethyl-2,3-dioxo-1-piperazinyl)carbonyl]amino]sulfonyl]amino]carbonyl]-2-oxo-3-azetidinyl]carbamic acid, phenylmethyl ester, potassium salt (548 mg) was hydrogenated in 50 ml of dimethylformamide in the presence of 270 mg of 10% palladium on charcoal for 45 minutes. To the hydrogenation solution, 210 mg of (Z)-2-amino-α-(methoxyimino)-4-thiazoleacetic acid, 50 mg of N-hydroxybenzotriazole and 300 mg of dicyclohexylcarbodiimide were added and the solution was stirred at 20° C. for 16 hours. The solvent was removed in vauco, the residue filtered with ethyl acetate and the crude compound was chromatographed on HP-20 resin using water/acetone (9:1) as eluent. Yield 280 mg.

EXAMPLE 27

[3S(Z)]-2-[[[2-[[1-[[[[(4-Ethyl-2,3-dioxo-1-piperazinyl)carbonyl]amino]sulfonyl]amino]carbonyl]-2-oxo-3-azetidinyl]-1-(2-amino-4-thiazolyl)-2-oxoethylidene]amino]oxy]-2-methylpropanoic acid, dipotassium salt (S)-[1-[[[[[(4-Ethyl-2,3-dioxo-1-piperazinyl)carbonyl]amino]sulfonyl]amino]carbonyl]-2-oxo-3-azetidinyl]carbamic acid, phenylmethyl ester, potassium salt (548 mg; see example 26A) was hydrogenated in 50 ml of dimethylformamide in the presence of 270 mg of 10% palladium on charcoal for 45 minutes. After removal of the catalyst, 450 mg of (Z)-2-amino-α-[[2-(diphenylmethoxy)-1,1-dimethyl-2-oxoethoxy]imino]-4-thiazoleacetic acid, 100 mg of N-hydroxybenzotriazole and 300 mg of dicyclohexylcarbodiimide were added. The solution was stirred for 16 hours. The solvent was removed in vacuo and the residue was filtered with ethyl acetate. The crude benzhydryl ester of the title compound was suspended in 2 ml of anisole, cooled to −10° C. and 4 ml of trifluoroacetic acid was dropped in with stirring. The temperature was maintained at −5° C. for 2 hours. Ether (100 ml) was added and the precipitate was filtered off, dried and dissolved in 5 ml of water, the pH adjusted to 6.5 and the solution chromatographed on HP-20 resin using water as eluent. The title compound (180 mg) was isolated by freeze drying.

EXAMPLE 28

[3S(R)]-4-Ethyl-N-[2-[[1-[[[[(methylamino)carbonyl]amino]sulfonyl]amino]carbonyl]-2-oxo-3-azetidinyl]amino]-2-oxo-1-phenylethyl-2,3-dioxo-1-piperazinecarboxamide, potassium salt (S)-[1-[[[[(Methylamino)carbonyl]amino]sulfonyl]amino]carbonyl]-2-oxo-3-azetidinyl]carbamic acid, phenylmethyl ester, potassium salt (437 mg; see example 17A) was hydrogenated in 50 ml of dry dimethylformamide in the presence of 200 mg of 10% palladium on charcoal for 45 minutes. The catalyst was filtered off, 350 mg of (R)-α-[[(4-ethyl-2,3-dioxo-1-piperazinyl)carbonyl]amino]benzeneacetic acid, 50 mg of N-hydroxybenzotriazole and 300 mg of dicyclohexylcarbodiimide were added; the solution was stirred for 12 hours. After removal of the solvent in vacuo, the residue was chromatographed on HP-20 resin using water/acetone (9:1) as eluent. Yield 380 mg; melting point 178°-183° C., dec.

EXAMPLE 29

[3S(Z)]-2-[[[1-(2-Amino-4-thiazolyl)-2-[[1-[[[[(methylamino)carbonyl]amino]sulfonyl]amino]carbonyl]-2-oxo-3-azetidinyl]amino]-2-oxoethylidene]amino]oxy]-2-methylpropanoic acid, dipotassium salt (S)-[1-[[[[(Methylamino)carbonyl]amino]sulfonyl]amino]carbonyl]-2-oxo-3-azetidinyl]carbamic acid, phenylmethyl ester, potassium salt (437 mg; see example 17A) was hydrogenated in 50 ml of dimethylformamide in the presence of 200 mg of 10% palladium on charcoal for 45 minutes. The catalyst was filtered off and 450 mg of (Z)-2-amino-α-[[2-(diphenylmethoxy)-1,1-dimethyl-2-oxoethoxy]imino]-4-thiazoleacetic acid, 50 mg of N-hydroxybenzotriazole and 300 mg of dicyclohexylcarbodiimide were added. The solution was stirred overnight, evaporated to dryness, the residue suspended in 2 ml of anisole, cooled to −10° C. and 4 ml of trifluoroacetic acid was dropped in. Stirring was continued for 2 hours at −5° C. After addition of 100 ml of ether, the precipitate was filtered off, dissolved in 5 ml of water, the pH adjusted to 6.5 with 1 N potassium hydroxide and the aqueous solution chromatographed on HP-20 resin using water as eluent. The title compound (280 mg) was isolated by freeze drying, melting point 215°-220° C., dec.

EXAMPLE 30

[3S(Z)]-2-Amino-N-[1-[[[[[(dimethylamino)carbonyl]amino]sulfonyl]amino]carbonyl]-2-oxo-3-azetidinyl]-α-(methoxyimino)-4-thiazoleacetamide, potassium salt (S)-[1-[[[[[(Dimethylamino)carbonyl]amino]sulfonyl]amino]carbonyl]-2-oxo-3-azetidinyl]carbamic acid, phenylmethyl ester, potassium salt (451 mg; see example 21A) was hydrogenated in 50 ml of dimethylformamide in the presence of 200 mg of 10% palladium on charcoal for 45 minutes. The catalyst was filtered off and 201 mg of (Z)-2-amino-α-(methoxyimino)-4-thiazoleacetic acid, 50 mg of N-hydroxybenzotriazole and 300 mg of dicyclohexylcarbodiimide were added. The solution was stirred for 12 hours at ambient temperature. The solvent was removed in vacuo and the crystalline residue chromatographed on HP-20 resin using water/acetone (9.5:0.5) as eluent. Yield 285 mg; melting point 201° C., dec.

EXAMPLE 31

[3S(Z)]-2-Amino-α-(methoxyimino)-N-[2-oxo-1-[[[[(2-oxo-1-pyrrolidinyl)carbonyl]amino]sulfonyl]amino]carbonyl]-3-azetidinyl]-4-thiazoleacetamide, potassium salt (A)

(S)-[2-Oxo-1-[[[[[(2-oxo-1-pyrrolidinyl)carbonyl]amino]sulfonyl]amino]carbonyl]-3-azetidinyl]carbamic acid, phenylmethyl ester, potassium salt (S)-3-[[(Phenylmethoxy)carbonyl]amino]-2-azetidinone (3 g) was suspended in 100 ml of dry tetrahydrofuran at 0° C. Chlorosulfonylisocyanate (2.1 g) was slowly dropped in with stirring while the temperature was maintained at 0° C.; after 30 minutes, a clear solution was obtained. At 0° C., 1.7 g of triethylamine and 2.05 g of N-carbamoylpyrrolidone were added. Stirring was continued at ambient temperature for 15 hours. After this time the precipitate was filtered off and the mother liquor evaporated to dryness. The residue was dissolved in 50 ml of water/acetone (1:1), the pH adjusted to 6.5 with 1 N potassium hydroxide, the acetone removed in vacuo and the remaining aqueous solution freeze dried yielding 6 g of the title compound.

(B)

[3S(Z)]-2Amino-α-(methoxyimino)-N-[2-oxo-1-[[[[[(2-oxo-1-pyrrolidinyl)carbonyl]amino]sulfonyl]amino]carbonyl]-3-azetidinyl]-4-thiazoleacetamide, potassium salt (S)-[2-Oxo-1-[[[[[(2-oxo-1-pyrrolidinyl)carbonyl]amino]sulfonyl]amino]carbonyl]-3-azetidinyl]carbamic acid, phenylmethyl ester, potassium salt (1 g) was hydrogenated in dimethylformamide using a 10% palladium on charcoal catalyst. The catalyst was filtered off, and 0.44 g of (Z)-2-amino-α-(methoxyimino)-4-thiazoleacetic acid, 30 mg N-hydroxybenzotriazole and 0.82 g dicyclohexylcarbodiimide were added to the mother liquor. The solution was stirred overnight, the solvent removed in vacuo and the residue chromatographed on HP-20 resin (eluting with water) yielding 300 mg of the title compound.

EXAMPLE 32

[3S(Z)]-2-[[[1-(2-Amino-4-thiazolyl)-2-oxo-2-[[2-oxo-1-[[[[[(2-oxo-1-pyrroldinyl)carbonyl]amino]sulfonyl]amino]carbonyl]-3-azetidinyl]amino]ethylidene]amino]oxy]-2-methylpropanoic acid, dipotassium salt (S)-[2-Oxo-1-[[[[[(2-oxo-1-pyrrolidinyl)carbonyl]amino]sulfonyl]amino]carbonyl]-3-azetidinyl]carbamic acid, phenylmethyl ester, potassium salt (1.5 g; see example 31A) was hydrogenated in dimethylformamide using a 10% palladium on charcoal catalyst. The catalyst was filtered off, and 1.47 g of (Z)-2-amino-α-[[2-(diphenylmethoxy)-1,1-dimethyl-2-oxoethoxy]imino]-4-thiazoleacetic acid, 40 mg of N-hydroxybenzotriazole and 1.26 g of dicyclohexylcarbodiimide were added to the mother liquor. The solution was stirred overnight, the solvent removed in vacuo and the residue filtered with ether. The residue was suspended in 5 ml of anisole and cooled to −5° C. Trifluoroacetic acid (13 ml) was slowly dropped in with stirring, and after 30 minutes the crude product was precipitated by the addition of 100 ml of ether and filtered off. The product was dissolved in 5 ml of water and the pH adjusted to 6.5 with 1 N potassium hydroxide. Chromatography on HP-20 resin (eluting with water) yielded 500 mg of the title compound, melting point 233° C., dec.

EXAMPLE 33

[3S(R)]-4-Ethyl-2,3-dioxo-N-[2-oxo-2-[[2-oxo-1[[[[[(2-oxo-1-pyrrolidinyl)carbonyl]amino]sulfonyl]amino]carbonyl]-3-azetidinyl]amino]-1-phenylethyl]-1-piperazinecarboxamide, potassium salt (S)-[2-Oxo-1-[[[[[(2-oxo-1-pyrroldinyl)carbonyl]amino]sulfonyl]amino]carbonyl]-3-azetidinyl]carbamic acid, phenylmethyl ester, potassium salt (1 g; see example 31A) was hydrogenated in dimethylformamide using a 10% palladium on charcoal catalyst. The catalyst was filtered off, 0.7 g of (R)-α-[[(4-ethyl-2,3-dioxo-1-piperazinyl)carbonyl]amino]benzeneacetic acid, 30 mg of N-hydroxybenzotriazole and 0.82 g of dicyclohexylcarbodiimide were added to the mother liquor, and the mixture was stirred overnight at ambient temperature. The solvent was removed in vacuo and the residue chromatographed on HP-20 resin, eluting with water, to yield 300 mg of the title compound, melting point 186° C.

EXAMPLE 34

[3S(Z)]-2-Amino-α-(methoxyimino)-N-[2-oxo-1-[[[[[(2-oxo-3-oxazolidinyl)carbonyl]amino]sulfonyl]amino]carbonyl]-3-azetidinyl]-4-thiazoleacetamide, potassium salt (A)

(S)-[2-Oxo-1-[[[[[(2-oxo-3-oxazolidinyl)carbonyl]amino]sulfonyl]amino]carbonyl]-3-azetidinyl]carbamic acid, phenylmethyl ester, potassium salt (S)-3-[[(Phenylmethoxy)carbonyl]amino]-2-azetidinone (3.0 g) was suspended in 300 ml of dry tetrahydrofuran and cooled to −70° C. Chlorosulfonylisocyanate (2.3 g) dissolved in 10 ml of dry tetrahydrofuran was dropped in with stirring. The temperature was allowed to rise to 0° C. and this temperature was maintained for 10 minutes. Afterwards it was cooled to −40° C. Triethylamine (1.65 g) and 1.95 g of N-carbamoyl-2-oxooxazolidine were added. The mixture was stirred at room temperature for 14 hours and the solvent was removed in vacuo. After dissolution in ethyl acetate, 100 ml of 2N phosphoric acid was added and extracted three times with ethyl acetate. The combined organic layers were evaporated in vacuo, the residue was dissolved in 100 ml of acetone/water (1:1) and the pH was adjusted to 6.5 with 1N potassium hydroxide. After removal of the acetone in vacuo, the aqueous solution was freeze dried yielding 5.2 g of crude product.

(B)

[3S(Z)]-2-Amino-α-(methoxyimino)-N-[2-oxo-1[[[[[(2-oxo-3-oxazolidinyl)carbonyl]amino]sulfonyl]amino]carbonyl]-3-azetidinyl]-4-thiazoleacetamide, potassium salt (S)-[2-Oxo-1-[[[[[(2-oxo-3-oxazolidinyl)carbonyl]amino]sulfonyl]amino]carbonyl]-3-azetidinyl]carbamic acid, phenylmethyl ester, potassium salt (1 g) was hydrogenated in 80 ml of dry dimethylformamide using 0.5 g of 10% palladium on charcoal as catalyst. After 20 minutes, the hydrogenation was completed and the catalyst was filtered off. (Z)-2-Amino-α-(methoxyimino)-4-thiazoleacetic acid (0.44 g), 30 mg of N-hydroxybenzotriazole and 0.91 g of dicyclohexylcarbodiimide were added to the mother liquor. The solution was stirred for 12 hours at room temperature, the solvent removed in vacuo and the 1.7 g residue was chromatographed using HP-20 resin and water as eluent, yielding 0.3 g of the title compound, melting point 208° C., dec.

Analysis for $C_{14}H_{15}KN_8O_9S_2$: C: 30.99; H: 2.79; N: 20.65; S: 11.82; K: 7.21; Found: C: 30.08; H: 3.13; N: 19.52; S: 10.34; K: 7.41.

EXAMPLE 35

[3S(R)]-4-Ethyl-2,3-dioxo-N-[2-oxo-2-[[2-oxo-1-[[[[[(2-oxo-3-oxazolidinyl)carbonyl]amino]sulfonyl]amino]carbonyl]-3-azetidinyl]amino]-1-phenylethyl]-1-piperazinecarboxamide, potassium salt (S)-[2-Oxo-1-[[[[[2-oxo-3-oxazolidinyl)carbonyl]amino]sulfonyl]amino]carbonyl]-3azetidinyl]carbamic acid, phenylmethyl ester, potassium salt (1 g; see example 34A) was hydrogenated in 80 ml of dry dimethylformamide using 0.5 g of a 10% palladium on charcoal catalyst. The catalyst was filtered off, 0.7 g of (R)-α-[[(4-ethyl-2,3-dioxo-1-piperazinyl)carbonyl]amino]benzeneacetic acid, 30 mg of N-hydroxybenzotriazole and 0.91 g of dicyclohexylcarbodiimide were added to the mother liquor, and the mixture was stirred for 14 hours at ambient temperature. The solvent was removed in vacuo and the residue chromatographed on HP-20 resin, eluting with water, to yield 0.36 g of the title compound, melting point 187° C., dec.

Analysis for $C_{23}H_{25}KN_8O_{11}S$: C: 41.81; H: 3.81; N: 16.96; S: 4.85; K: 5.92. Found: C: 40.04; H: 3.93; N: 16.33; S: 4.45; K: 5.59.

EXAMPLE 36

[3S(Z)]-2-[[[1-(2-Amino-4-thiazolyl)-2-oxo-2-[[2-oxo-1-[[[[[(2-oxo-3-oxazolidinyl)carbonyl]amino]sulfonyl]amino]carbonyl]-3-azetidinyl]amino]ethylidene]amino]oxy]-2-methylpropanoic acid, dipotassium salt (S)-[2-Oxo-1-[[[[[(2-oxo-3-oxazolidinyl)carbonyl]amino]sulfonyl]amino]carbonyl]-3-azetidinyl]carbamic acid, phenylmethyl ester, potassium salt (1 g; see example 34A) was hydrogenated in 80 ml of dimethylformamide using 0.5 g of a 10% palladium on charcoal catalyst. The catalyst was filtered off, and 0.97 g of (Z)-2-amino-α-[[2-(diphenylmethoxy)1,1-dimethyl-2-oxoethoxy]imino]-4-thiazoleacetic acid, 30 mg of N-hydroxybenzotriazole and 0.91 g of dicyclohexylcarbodiimide were added to the mother liquor. The solution was stirred for 14 hours and the solvent removed in vacuo. The residue was suspended in 4 ml of anisole and cooled to −5° C. Trifluoroacetic acid (12 ml) was slowly dropped in with stirring, and after 20 minutes the crude product was precipitated by the addition of 100 ml of ether and filtered off. The product was dissolved in 20 ml of water/acetone (1:1) and the pH adjusted to 6.5 with 1N potassium hydroxide. Acetone was evaporated, the residue was freeze-dried and the crude product was chromatography on HP-20 resin to yield 0.28 g of the title compound, melting point 250° C., dec.

Analysis for $C_{17}H_{18}K_2N_8O_{11}S_2$: C: 31.28; H, 2.78 N: 17.17; S: 9.83; K: 11.98. Found: C: 29.54; H: 3.23; N: 16.93; S: 8.97; K: 11.86.

Example 37

[3S(Z)]-2-Amino-N-[1-[[[[[3-(2-aminoethyl)-2-oxo-1-imidazolidinyl]carbonyl]amino]sulfonyl]amino]carbonyl]-2-oxo-3-azetidinyl]-α-(methoxyimino)-4-thiazoleacetamide, potassium salt (S)-3-[[(Phenylmethoxy)carbonyl]amino]-2azetidinone (2 g) was suspended in 200 ml of dry tetrahydrofuran and cooled to −70° C. Chlorosulfonylisocyanate (1.4 g) dissolved in 7 ml of dry tetrahydrofuran was added with stirring. The temperature was allowed to rise to 0° C. and this temperature was maintained for 10 minutes. Afterwards it was cooled to −40° C., 1.2 g of triethylamine was dropped in and 2.9 g of 1-[2-[(t-butoxycarbonyl)amino]ethyl]-3-carbamoyl-2-oxoimidazolidine was added. This mixture was stirred at room temperature for 14 hours. Following the work-up procedure described in example 34A yielded 5.4 g of (S)-[1-[[[[[3-[2-(t-butoxycarbonylamino)ethyl]-2-oxo-1-imidazolidinyl]carbonyl]amino]sulfonyl]amino]carbonyl]-2-oxo-3azetidinyl]carbamic acid, phenylmethyl ester, potassium salt.

The above-prepared compound (2.7 g) was hydrogenated in 250 ml of dry dimethylformamide using 1.4 g of 10% palladium on charcoal catalyst. After 30 minutes the hydrogenation was completed and the catalyst was filtered off. (Z)-2-Amino-α-(methoxyimino) -4-thiazoleacetic acid (0.95 g), 54 mg of N-hydroxybenzotriazole and 1.75 g of dicyclohexylcarbodiimide were added to the mother liquor. The solution was stirred for 12 hours at room temperature, the solvent removed in vacuo and the residue dissolved in 6 ml of anisole and cooled to −5° C. Trifluoroacetic acid (15 ml) was carefully dropped in with stirring. The temperature was maintained for an additional 3 hours, and the title compound precipitated by the addition of 150 ml of dry ether. The product was filtered and dissolved in 30 ml of water/acetone (1:1), and the pH was adjusted to 6.5 by the addition of 1N potassium hydroxide. Acetone was evaporated, the residue freeze-dried and 2.7 g of crude product was chromatographed on HP-20 resin eluting with water, to yield 0.25 g of the title compound, melting point 193° C., dec.

EXAMPLE 38

[3S(Z)]-2-[[[2-[[1-[[[[[3-(2-Aminoethyl)-2-oxo-1-imidazolidinyl]carbonyl]amino]sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt (S)-[1-[[[[[3-[2-(t-Butoxycarbonylamino)ethyl]-2-oxo-1-imidazolidinyl]carbonyl]amino]sulfonyl]amino]carbonyl]-2-oxo-3-azetidinyl]carbamic acid, phenylmethyl ester, potassium salt (2.7 g; see example 37) was hydrogenated in dry dimethylformamide using 10% palladium on charcoal as a catalyst. The catalyst was filtered off, and (Z)-2-amino-α-[[2-(diphenylmethoxy) -1,1-dimethyl-2-oxoethoxy]imino]-4thiazoleacetic acid (2.1 g), 54 mg of N-hydroxybenzotriazole and 1.75 g of dicyclohexylcarbodiimide were added to the mother liquor. Following the work-up procedure described in example 37 and chromatography on HP-20 resin eluting with water yielded 0.3 g of the title compound, melting point 221° C., dec.

EXAMPLE 39

3S(Z)]-2-Amino-N-[1-[[[[[3-(2-hydroxyethyl)-2-oxo-1-imidazolidinyl]carbonyl]amino]sulfonyl]amino]carbonyl]-2-oxo-3-azetidinyl]-α-(methoxyimino) -4-thiazoleacetamide, potassium salt (S)-3-[[(Phenylmethoxy)carbonyl]amino]-2-azetidinone (1.5 g) was suspended in 100 ml of dry tetrahydrofuran and cooled to -70° C. Chlorosulfonylisocyanate (1.1 g) dissolved in 10 ml of dry tetrahydrofuran was dropped in with stirring. The temperature was allowed to rise to 0° C. and maintained there for 20 minutes, followed by cooling to −40° C. Triethylamine (0.9 g) and 2.8 g of 1-carbamoyl-2-oxo-3-[2-[(triphenylmethyl)oxy]ethyl]imidazolidine were added and the mixture was stirred at room temperature for 14 hours. The solvent was removed in vacuo and the work-up procedure of example 34A was followed yielding 4.3 g of (S)-[1-[[[[[3-(2-hydroxyethyl)-2-oxo-1-imidazolidinyl]carbonyl]amino]sulfonyl]amino]carbonyl]-2-oxo-3-azetidinyl]carbamic acid, phenylmethyl ester, potassium salt.

The above-prepared compound was hydrogenated in 80 ml of dry dimethylformamide using 0.3 g of 10% palladium on charcoal catalyst. After 30 minutes the hydrogenation was completed and the catalyst was filtered off. (Z)-2-Amino-α-(methoxyimino) -4-thiazoleacetic acid (195 mg), 13 mg of N-hydroxybenzotriazole and 360 mg of dicyclohexylcarbodiimide were added to the mother liquor. The solution was stirred for 12 hours at room temperature, the solvent removed in vacuo and the residue precipitated with ether. Crude product (0.5 g) was purified on HP-20 resin (eluent water/acetone (9.5:0.5)) yielding 30 mg of the title compound, melting point 193° C., dec.

Analysis for $C_{16}H_{19}KN_9O_9S_2$: C: 32.87; H: 3.28; N: 21.56; S: 10.97; K: 6.69. Found: C: 31.26; H: 3.44; N: 18.56; S: 8.86; K: 6.56.

Example 40

[3S(Z)]-2-[[[1-(2-Amino-4-thiazolyl)-2-[[1[[[[[3-(2-hydroxyethyl)-2-oxo-1-imidazolidinyl]carbonyl]amino]sulfonyl]amino]carbonyl]-2-oxo-3-azetidinyl]amino]-2-oxoethylidene]amino]oxy]-2methylpropanoic acid, dipotassium salt (S)-[1-[[[[[3-(2-Hydroxyethyl)-2-oxo-1-imidazolidinyl]carbonyl]amino]sulfonyl]amino]carbonyl]-2-oxo-3-azetidinyl]carbamic acid, phenylmethyl ester, potassium salt (470 mg; see example 39) was hydrogenated in 80 ml of dry dimethylformaide using 0.3 g of 10% palladium on charcoal as a catalyst. After 30 minutes the catalyst was filtered off, and (Z)-2-amino-α-[[2-(diphenylmethoxy)-1,1-dimethyl-2-oxoethoxy]imino]-4-thiazoleacetic acid, 13 mg of N-hydroxybenzotriazole and 360 mg of dicyclohexylcarbodiimide were added to the mother liquor. Following the procedure described in example 36 yielded the title compound, melting point 219° C., dec.

EXAMPLE 41

[3S(Z)]-2-[[[2-[[[[[(3-Amino-2-oxo-1-imidazolidinyl)carbonyl]amino]sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt (A)

(S)-[1-[[[[[3-[(t-Butoxycarbonyl)amino]-2-oxo-1-imidazolidinyl]carbonyl]amino]sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (1.5 g) were suspended in 150 ml of dry tetrahydrofuran and cooled to −60° C. Chlorosulfonylisocyanate (1.1 g) dissolved in 20 ml of dry tetrahydrofuran was dropped in with stirring. The temperature was allowed to rise to 0° C. and this temperature was maintained for 15 minutes and then cooled to −60° C. Triethylamine (0.9 g) and 1.7 g of 1-carbamoyl-3-[(t-butoxycarbonyl)amino]-2-oxoimidazolidine were added. The mixture was stirred at room temperature for 14 hours and then worked-up using the procedure described in example 34, part A, yielding 1.5 g of the title compound.

(B)
[3S(Z)]-2-[[[2-[[1-[[[[(3-Amino-2-oxo-1-imidazolidinyl)carbonyl]amino]sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt (S)-[1-[[[[[3-[(t-Butoxycarbonyl)amino]-2-oxo -1-imidazolidinyl]carbonyl]amino]sulfonyl]amino]carbonyl]-2-oxo-3-azetidinyl]carbamic acid, phenylmethyl ester, potassium salt (0.79 g) was hydrogenated in 60 ml of dry dimethylformamide using 0.4 g of 10% palladium on charcoal catalyst. After 20 minutes the hydrogenation was completed and the catalyst was filtered off. (Z)-2-Amino-α-[[2-(diphenylmethoxy)-1,1-dimethyl-2-oxoethoxy]imino]-4-thiazoleacetic acid (0.63 g), 19 mg of N-hydroxybenzotriazole and 540 mg of dicyclohexylcarbodiimide were added to the mother liquor. Following the procedure described in example 34B, yielded 48 mg of the title compound, melting point 208° C., dec.

EXAMPLE 42

[3S(Z)]-2-Amino-α-(methoxyimino)-N-[1-[[[[[3-[(1-methylethylidene)amino]-2-oxo-1-imidazolidinyl]carbonyl]amino]sulfonyl]amino]carbonyl]-2-oxo-3-azetidinyl]-4-thiazoleacetamide, potassium salt (S)-[1-[[[[[3-[(t-Butoxycarbonyl)amino]-2-oxo -1-imidazolidinyl]carbonyl]amino]sulfonyl]amino]carbonyl]-2-oxo-3-azetidinyl]carbamic acid, phenylmethyl ester, potassium salt (0.7 g; see example 41A) was hydrogenated and then reacted with 0.26 g of (Z)-2-amino-α-(methoxyimino)-4-thiazoleacetic acid following the procedures described in example 37B, yielding 65 mg of the title compound, melting point 207° C., dec.

Analysis for $C_{17}H_{21}KN_{10}O_8S_2$: C: 34.22; H: 3.55; N: 23.47; S: 10.75; K: 6.55. Found: C: 32.56; H: 3.88; N: 21.37; S: 9.10; K: 7.03.

EXAMPLE 43

[3S(Z)]-2-Amino-N-[1-[[[[[(3-methyl-2-oxo-1-imidazolidinyl)carbonyl]amino]sulfonyl]amino]carbonyl]-2-oxo-3-azetidinyl]-α-(methoxyimino)-4-thiazoleacetamide, potassium salt (A)

(S)-[1-[[[[(3-Methyl-2-oxo-1-imidazolidinyl)carbonyl]amino]sulfonyl]amino]carbonyl]-2-oxo-3-azetidinyl]-carbamic acid, phenylmethyl ester, potassium salt (S)-3-[[(Phenylmethoxy)carbonyl]amino]-2-azetidinone (3.0 g) was suspended in 300 ml of dry tetrahydrofuran and cooled to −70°0 C. Chlorosulfonylisocyanate (2.1 g) dissolved in 10 ml of dry tetrahydrofuran was dropped in with stirring. The temperature was allowed to rise to 0° C. and this temperature was maintained for 10 minutes, then cooled to −40° C. Triethylamine (1.7 g) and 2.3 g of 1-carbamoyl-3-methyl-2-oxoimidazolidine were added. Following the procedure described in example 34A yielded 4.3 g of the title compound.

(B)
[3S(Z)]-2-Amino-N-[[[[[(3-methyl-2-oxo-1-imidazolidinyl)carbonyl]amino]sulfonyl]amino]carbonyl]-2-oxo-3-azetidinyl]-α-(methoxyimino)-4-thiazoleacetamide, potassium salt (S)-[1-[[[[(3-Methyl-2-oxo-1-imidazolidinyl)carbonyl]amino]sulfonyl]amino]carbonyl]-2-oxo-3azetidinyl]carbamic acid, phenylmethyl ester, potassium salt (1.2 g) was hydrogenated in 80 ml of dry dimethylformamide using 0.6 g of 10% palladium on charcoal as catalyst. After 30 minutes the catalyst was filtered off, and (Z)-2-amino-α-(methoxyimino) -4-thiazoleacetic acid (0.52 g), 32 mg of N-hydroxybenzotriazole and 1.0 g of dicyclohexylcarbodiimide were added to the mother liquor. The solution was stirred for 13 hours at room temperature and the solvent was then removed in vacuo. The residue was chromatographed on HP-20 resin, eluting with water, to yield 0.120 g of the title compound, melting point 205° C.,dec.

Analysis for $C_{15}H_{18}KN_9O_8S_2$: C: 32.43; H: 3.27; N: 22.69; S: 11.54; K: 7.04. Found: C: 30.83; H: 3.44; N: 21.34; S: 10.20; K: 7.30.

EXAMPLE 44

[3S(Z)]-2-[[[2-[[1-[[[[[(3-Methyl-2-oxo-1-imidazolidinyl)carbonyl]amino]sulfonyl]amino]carbonyl]2-oxo-3-azetidinyl]amino]-1-(2-amino-4-thiazolyl) -2-oxoethylidene]amino]oxy]-2-methylpropanoic acid, dipotassium salt (S)-[1-[[[[[(3-Methyl-2-oxo-1-imidazolidinyl)carbonyl]amino]sulfonyl]amino]carbonyl]-2-oxo-3-azetidinyl]carbamic acid, phenylmethyl ester, potassium salt (1.5 g; see example 43A) was hydrogenated in 80 ml of dry dimethylformamide using 0.8 g of 10% palladium on charcoal as catalyst. After 30 minutes the catalyst was filtered off and 1.4 g of (Z)-2-amino-α-[[2-(diphenylmethoxy) -1,1-dimethyl-2-oxoethoxy]imino]-4-thiazoleacetic acid, 40 mg of N-hydroxybenzotriazole and 1.3 g of dicyclohexylcarbodiimide were added to the mother liquor. Following the procedure of ecample 36 yielded 0.5 g of the title compound, melting point 211° C., dec.

Analysis for $C_{18}H_{21}K_2N_9O_{10}S_2$: C: 32.47; H: 3.18; N: 18.94; S: 9.63; K: 11.75. Found: C: 30.55; H: 3.53; N: 18.12; S: 8.65; K: 10.97.

EXAMPLE 45

[3S(Z)]-2-[[[2-[[1-[[[[[(2-Oxo-1-imidazolidinyl)carbonyl]amino]sulfonyl]amino]carbonyl]-2-oxo-3-azetidinyl-]amino]-1-(2-amino-4-thiazolyl)-2-oxoethylidene]amino]oxy]-2-methylpropanoic acid, dipotassium salt (A)

(S)-[1-[[[[[[2-Oxo-3-(triphenylmethyl)-1imidazolidinyl]-carbonyl]amino]sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (1.3 g) was suspended in 130 ml of dry tetrahydrofuran and cooled to −70° C. Chlorosulfonylisocyanate (0.9 g) dissolved in 5 ml of dry tetrahydrofuran was dropped in with stirring. The temperature was allowed to rise to 0° C. and maintained there for 10 minutes, followed by cooling to −40° C. Triethylamine (0.8 g) and 0.65 g of ·1-carbamoyl-2-oxo-3-(triphenylmethyl-)imidazolidine were added and the mixture was worked-up following the procedure described in example 34A to yield 3.2 g of the title compound.

(B)

[3S(Z)]-2-[[[2-[[1-[[[[[(2-Oxo-1-imidazolidinyl)carbonyl-]amino]sulfonyl]amino]carbonyl]-2-oxo-3-azetidinyl-]amino]-1-(2-amino-4-thiazolyl)-2-oxoethylidene]amino]oxy]-2-methylpropanoic acid, dipotassium salt (S)-[1-[[[[[[2-Oxo-3-(triphenylmethyl)-1-imidazolidinyl]carbonyl]amino]sulfonyl]amino]carbonyl]-2-oxo-3-azetidinyl]carbamic acid, phenylmethyl ester, potassium salt (1.5 g) was hydrogenated in 80 ml of dry dimethylformamide using 0.9 g of 10% palladium on charcoal as catalyst. After 30 minutes the catalyst was filtered off and 0.98 g of (Z)-2-amino-α-[[2-(diphenylmethoxy) -1,1-dimethyl-2-oxoethoxy]imino]-4-thiazoleacetic acid, 27 mg of N-hydroxybenzotriazole and 0.84 g of dicyclohexylcarbodiimide were added to the mother liquor. Following the procedure of example 36 yielded 0.28 g of the title compound, melting point 228° C., dec.

EXAMPLE 46

[3S(Z)]-2-Amino-N-[1-[[[[[(2-oxo-1-imidazolidinyl)carbonyl]amino]sulfonyl]amino]carbonyl]-2-oxo-3-azetidinyl]-α-(methoxyimino)-4-thiazoleacetamide, potassium salt (A)

(S)-[1-[[[[[(2-Oxo-1-imidazolidinyl)carbonyl]amino]sulfonyl]amino]carbonyl]-2-oxo-3-azetidinyl]carbamic acid, phenylmethyl ester, potassium salt (S)-[1-[[[[[[2-Oxo-3-(triphenylmethyl)-1-imidazolidinyl]carbonyl]amino]sulfonyl]amino]carbonyl]-2-oxo-3-azetidinyl]carbamic acid, phenylmethyl ester, potassium salt (1.7 g; see example 45A) was treated with 2N phosphoric acid and 1N potassium hydroxide following the procedure described in example 34A to yield 1.73 g of the title compound.

(B)

[3S(Z)-2-Amino-N-[1-[[[[[(2-oxo-1-imidazolidinyl)carbonyl]amino]sulfonyl]amino]carbonyl]-2-oxo-3-azetidinyl]-α-(methoxyimino)-4-thiazoleacetamide, potassium salt (S)-[1-[[[[[(2-Oxo-1-imidazolidinyl)carbonyl]amino]sulfonyl]amino]carbonyl]-2-oxo-3-azetidinyl]carbamic acid, phenylmethyl ester, potassium salt (0.8 g) was hydrogenated in 70 ml of dry dimethylformamide using 0.5 g of 10% palladium on charcoal as catalyst. After 20 minutes the catalyst was filtered off, and (Z)-2-amino-α-(methoxyimino) -4-thiazoleacetic acid (0.38 g), 27 mg of N-hydroxybenzotriazole and 0.78 g of dicyclohexylcarbodiimide were added to the mother liquor. The solution was stirred for 14 hours at room temperature and the solvent was then removed in vacuo. The residue was chromatographed on HP-20 resin, to yield 200 mg of the title compound, melting point 216° C., dec.

EXAMPLE 47

[3S(Z)]-2-Amino-N-[1-[[[[[3-(methylsulfonyl)-2-oxo-1-imidazolidinyl]carbonyl]amino]sulfonyl]amino]carbonyl]-2-oxo-3-azetidinyl]-α-(methoxyimino)-4-thiazoleacetamide, potassium salt (A)

(S)-[1-[[[[[3-(Methylsulfonyl-2-oxo-1-imidazolidinyl]-carbonyl]amino]sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (3.0g) was suspended in 300 ml of dry tetrahydrofuran and cooled to −70° C. Chlorosulfonylisocyanate (2.1 g) dissolved in 10 ml of dry tetrahydrofuran was dropped in with stirring. The temperature was allowed to rise to 0° C. and this temperature was maintained for 10 minutes, then cooled to −40° C. Triethylamine (1.7 g) and 2.3 g of 1-carbamoyl-3-(methylsulfonyl) -2-oxoimidazolidine were added. Following the procedure described in example 34A yielded 2.8 g of the title compound.

(B)

[3S(Z)]-2-Amino-N-[1-[[[[[3-(methylsulfonyl)-2-oxo-1-imidazolidinyl]carbonyl]amino]sulfonyl]amino]carbonyl-2-oxo-3-azetidinyl]-α-(methoxyimino)-4-thiazoleacetamide, potassium salt (S)-[1-[[[[[3-(Methylsulfonyl)-2-oxo-1-imidazolidinyl]carbonyl]amino]sulfonyl]amino]carbonyl]-2-oxo-3-azetidinyl]carbamic acid, phenylmethyl ester, potassium salt (1.8 g) was hydrogenated in 300 ml of dry dimethylformamide using 2.0 g of 10% palladium on charcoal as catalyst. After 20 minutes the catalyst was filtered off, and (Z)-2-amino-α-(methoxyimino)-4-thiazoleacetic acid (1.1 g), 70 mg of N-hydroxybenzotriazole and 2.0 g of dicyclohexylcarbodiimide were added to the mother liquor. The solution was stirred for 12 hours at room temperature and the solvent was then removed in vacuo. The residue was chromatographed on HP-20 resin, eluting with water/acetone (9:1), to yield 200 mg of the title compound, melting point 204° C., dec.

EXAMPLE 48

[3S(Z)]-2-[[[2-[[1-[[[[[3-(Methylsulfonyl)-2-oxo -1-imidazolidinyl]carbonyl]amino]sulfonyl]amino]carbonyl]-2-oxo-3-azetidinyl]amino]-1(2-amino-4-thiazolyl)-2-oxoethylidene]amino]oxy]-2-methylpropanoic acid, dipotassium salt (S)-[1-[[[[[3-(Methylsulfonyl)-2-oxo-1-imidazolidinyl]carbonyl]amino]sulfonyl]amino]carbonyl]-2-oxo-3-azetidinyl]carbamic acid, phenylmethyl ester, potassium salt (1.5 g; see example 47A) was hydrogenated in 150 ml of dry dimethylformamide using 0.9 g of 10% palladium on charcoal as catalyst. After 20 minutes the catalyst was filtered off and 1.23 g of (Z)-2-amino-α-[[2-(diphenylmethoxy)-1,1-dimethyl-2-oxoethoxy]imino]-4-thiazoleacetic acid, 40 mg of N-hydroxybenzotriazole and 1.1 g of dicyclohexylcarbodiimide were added to the mother liquor. Following the procedure of example 36 yielded 180 mg of the title compound, melting point 236° C., dec.

EXAMPLE 49

[3S(Z)]-2-Amino-N-[1-[[[[[(3-isopropyl-2-oxo-1-imidazolidinyl)carbonyl]amino]sulfonyl]amino]carbonyl]-2-oxo-3-azetidinyl]-α-(methoxyimino)-4-thiazoleacetamide, potassium salt (A)

(S)-[1-[[[[[(3-Isopropyl-2-oxo-1-imidazolidinyl)carbonyl]amino]sulfonyl]amino]carbonyl]-2-oxo-3-azetidinyl]carbamic acid, phenylmethyl ester, potassium salt (S)-3-[[(Phenylmethoxy)carbonyl]amino]-2-azetidinone (3.0g) was suspended in 300 ml of dry tetrahydrofuran and cooled to −70° C. Chlorosulfonylisocyanate (2.1 g) dissolved in 10 ml of dry tetrahydrofuran was dropped in with stirring. The temperature was allowed to rise to 0° C. and this temperature was maintained for 10 minutes, then cooled to −40° C. Triethylamine (1.7 g) and 2.74 g of 1-carbamoyl-3-isopropyl-2-oxoimidazolidine were added. Following the procedure described in example 34A yielded 5.9 g of the title compound.

(B) [3S(Z)]-2-Amino-N-[1-[[[[[(3-isopropyl-2-oxo -1-imidazolidinyl)carbonyl]amino]sulfonyl]amino]carbonyl]-2-oxo-3-azetidinyl]-α-(methoxyimino)-4-thiazoleacetamide, potassium salt (S)-[1-[[[[[(3-Isopropyl-2-oxo-1-imidazolidinyl)carbonyl]amino]sulfonyl]amino]carbonyl]-2-oxo-3azetidinyl]carbamic acid, phenylmethyl ester, potassium salt (1.5 g) was hydrogenated in 150 ml of dry dimethylformamide using 0.8 g of 10% palladium on charcoal as catalyst. After 20 minutes the catalyst was filtered off, and 0.6 g of (Z)-2-amino-α-(methoxyimino)-4-thiazoleacetic acid, 40 mg of N-hydroxybenzotriazole and 1.2 g of dicyclohexylcarbodiimide were added to the mother liquor. The solution was stirred for 14 hours at room temperature and the solvent was then removed in vacuo. The residue was chromatographed on HP-20 resin, eluting with water/acetone (9.25:0.75) to yield 300 mg of the title compound, melting point 189° C., dec.

EXAMPLE 50

[3S(Z)]-2-[[[2-[[1-[[[[[(3-isopropyl-2-oxo-1-imidazolidinyl)carbonyl]amino]sulfonyl]amino]carbonyl]-2-oxo-3-azetidinyl]amino]-1-(2-amino-4-thiazolyl) -2-oxoethylidene]amino]oxy]-2-methylpropanoic acid, dipotassium salt (S)-[1-[[[[[(3-Methyl-2-oxo-1-imidazolidinyl)carbonyl]amino]sulfonyl]amino]carbonyl]-2-oxo-3azetidinyl]carbamic acid, phenylmethyl ester, potassium salt (1.5 g; see example 43A) was hydrogenated in 150 ml of dry dimethylformamide using 0.8 g of 10% palladium on charcoal as catalyst. After 20 minutes the catalyst was filtered off and 1.3 g of (Z)-2-amino-α-[[2-(diphenylmethoxy) -1,1-dimethyl-2-oxoethoxy]imino]-4-thiazoleacetic acid, 40 mg of N-hydroxybenzotriazole and 1.2 g of dicyclohexylcarbodiimide were added to the mother liquor. Following the procedure of example 36 yielded 0.4 g of the title compound, melting point 234° C., dec.

What is claimed is:

1. A compound having the formula

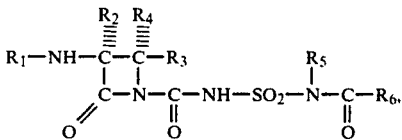

or a pharmaceutically acceptable salt thereof, wherein
$R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, aryl or a 5, 6 or 7-membered heterocycle or one of $R_3$ and $R_4$ is hydrogen and the other is azido, halomethyl, dihalomethyl, trihalomethyl, alkoxycarbonyl, 2-phenylethenyl, 2-phenylethynyl, carboxyl,

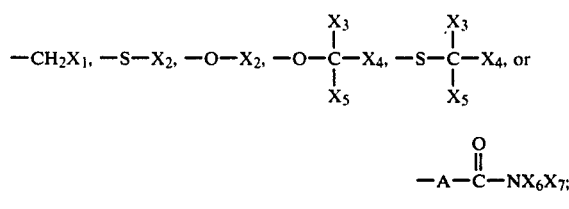

$X_1$ is azido, amino, hydroxy, alkanoylamino, alkylsulfonyloxy, arylsulfonyloxy, aryl, cyano, $-S-X_2$ or $-O-X_2$;
$X_2$ is alkyl, substituted alkyl, aryl, arylalkyl, alkanoyl, substituted alkanoyl, arylcarbonyl or heteroarylcarbonyl;
one of $X_3$ and $X_4$ is hydrogen and other is hydrogen or alkyl, or $X_3$ and $X_4$ when taken together with the carbon atom to which they are attached form a cycloalkyl group;

X₅ is formyl, alakanoyl, arylcarbonyl, arylalkylcarbonyl, carboxyl, alkoxycarbonyl, aminocarbonyl, (substituted amino)carbonyl, or cyano;

A is —CH=CH—, —CH₂—CH=CH—, —(CH₂)ₘ—, —(CH₂)ₘ'—O—, —(CH₂)ₘ'—NH—, —(CH₂)ₘ'—S—CH₂—, or —(CH₂)ₘ'—O—CH₂—;

m is 0, 1, 2 or 3;

m' is 1 or 2;

X₆ and X₇ are the same or different and each is hydrogen or alkyl, or X₆ is hydrogen and X₇ is amino, substituted amino, acylamino or alkoxy;

R₅ is hydrogen, alkyl aryl;

R₆ is hydrogen, alkyl, aryl, a 5, 6 or 7-membered heterocycle, —NR₇R₈, or —(CH₂)ₙ—X wherein n is 1, 2, 3 or 4 and X is halogen, aryl, alkoxy, aryloxy or —NR₉R₁₀;

R₇ and R₈ are the same or different and each is hydrogen, alkyl or aryl, or R₇ is hydrogen and R₈ is a 5, 6 or 7-membered heterocycle or —(CH₂)ₙ—Y wherein n is 1, 2, 3 or 4 and Y is alkoxy, amino, alkylthio or halogen; and R₉ and R₁₀ are the same or different and each is hydrogen or alkyl, or R₉ is hydrogen and R₁₀ is a 5, 6 or 7-membered heterocycle;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", and "alkynyl" refer to groups having 2 to 10 carbon atoms;

the term "aryl" refers to a phenyl or phenyl substituted with 1, 2 or 3 amino, halogen, hydroxyl, trifluoromethyl, alkyl of 1 to 4 carbon atoms, alkoxy of 1 to 4 carbon atoms or carboyl groups;

the term "substituted alkyl" refers to alkyl groups substituted with one, or more azido, amino, halogen, hydroxy, carboxy, cyano, alkoxycarbonyl, aminocarbonyl, alkanoyloxy, alkoxy, aryloxy, a 5, 6 or 7-membered heterocycleoxy, mercapto, alkylthio, arylthio, alkylsulfinyl, or alkylsulfonyl groups;

the term "substituted alkanoyl" refers to groups having the formula

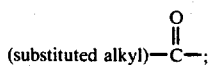

the term "substituted amino" refers to a group having the formula -NY₁Y₂ wherein Y₁ is hydrogen, alkyl, aryl, or arylalkyl, and Y₂ is alkyl, aryl, arylalkyl, hydroxy, cyano, alkoxy, phenylalkoxy, or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one, or more, halogen, hydroxy, nitro, amino, cyano, trifluoromethyl, alkyl of 1 to 4 carbon atoms, alkoxy of 1 to 4 carbon atoms, alkylsulfonyl, aryl, 2-furylmethyleneimino, phenylmethyleneimino or substituted alkyl, whereint he alkyl group has 1 to 4 carbon atoms, groups; and the term "a 5, 6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, piperidinyl, piperazinyl, imidazolidinyl, oxazolidinyl, pyrrolidinyl, tetrahydropyrimidinyl, dihydrothiazolyl, or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, aryl, 2-furylmethyleneimino, phenylmethyleneimino, or substituted alkyl, wherein the alkyl group has 1 to 4 carbon atoms, groups.

2. A compound in accordance with claim 1 wherein R₂ is hydrogen.

3. A compound in accordance with claim 1 wherein R₅ is hydrogen.

4. A compound in accordance with claim 1 wherein R₃ and R₄ are each hydrogen.

5. A compound in accordance with claim 1 wherein R₂, R₃, R₄ and R₅ are each hydrogen.

6. A compound in accordance with claim 5 wherein R₆ is hydrogen.

7. A compound in accordance with claim 5 wherein R₆ is alkyl.

8. A compound in accordance with claim 5 wherein R₆ is aryl.

9. A compound in accordance with claim 5 wherein R₆ is a 5,6 or 7-membered heterocycle.

10. A compound in accordance with claim 9 wherein R₆ is 4-alkyl-2,3-dioxo-1-piperazinyl.

11. A compound in accordance with claim 9 wherein R₆ is 2-oxo-1-imidazolidinyl.

12. A compound in accordance with claim 9 wherein R₆ is 3-alkyl-2-oxo-1-imidazolidinyl.

13. A compound in accordance with claim 9 wherein R₆ is 3-(substituted alkyl)-2-oxo-1-imidazolidinyl.

14. A compound in accordance with claim 13 wherein R₆ is 3-(2-aminoethyl)-2-oxo-1-imidazolidinyl.

15. A compound in accordance with claim 5 wherein R₁ is (Z)-2-amino-α-(alkoxyimino)-4-thiazoleacetyl.

16. A compound in accordance with claim 15 wherein R₁ is (Z)-2-amino-α-(methoxyimino)-4-thiazoleacetyl.

17. A compound in accordance with claim 5 wherein R₁ is (Z)-2-amino-α-[(1-carboxy-1-methylethoxy)imino]-4-thiazoleacetyl.

18. A compound in accordance with claim 1: [3S(Z)]-2-[[[1-(2-amino-4-thiazolyl)-2-[[1-[[[[[(3-ethyl-2-oxo-1-imidazolidinyl)carbonyl]amino]sulfonyl]amino]carbonyl]-2-oxo-3-azetidinyl]amino]-2-oxoethylidene]amino]oxy]-2-methylpropanoic acid, or a salt thereof.

19. The compound in accordance with claim 18: [3S(Z)]-2-[[[1-(2-amino-4-thiazolyl)-2-[[1-[[[[[(3--ethyl-2-oxo-1-imidazolidinyl)carbonyl]amino]sulfonyl]amino]carbonyl-2-oxo-3-azetidinyl]amino]-2-oxoethylidene]amino]oxy]-2-methylpropanoic acid, dipotassium salt.

20. A compound in accordance with claim 1: [3S(Z)]-2-[[[2-[[1-[[[[[3-(2-aminoethyl)-2-oxo-1-imidazolidinyl]carbonyl]amino]sulfonyl]amino]carbonyl]-2-oxo-3-azetidinyl]amino]-1-(2-amino-4-thiazolyl)-2-oxoethylidene]amino]oxy]-2-methylpropanoic acid, or a salt thereof.

21. The compound in accordance with claim 20: [3S(Z)]-2-[[[2-[[1-[[[[[3-(2-aminoethyl)-2-oxo-1-imidazolidinyl]carbonyl]amino]sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt.

22. A compound in accordance with claim 1: [3S(Z)]-2-[[[2-[[1-[[[[[(3-methyl-2-oxo-1-imidazolidinyl)carbonyl]amino]sulfonyl]amino]carbonyl]-2-oxo-3-azetidinyl]amino]-1-(2-amino-4-thiazolyl) -2-oxoethylidene]amino]oxy]-2-methylpropanoic acid, or a salt thereof.

23. The compound in accordance with claim 22: [3S(Z)]-2-[[[2-[[1-[[[[[(3-methyl-2-oxo-1-imidazolidinyl)carbonyl]amino]sulfonyl]amino]carbonyl]-2-oxo-3-azetidinyl]amino]-1-(2-amino-4-thiazolyl) -2-oxoethylidene]amino]oxy]-2-methylpropanoic acid, dipotassium salt.

24. A compound in accordance with claim 1: [3-S(Z)]-2-[[[2-[[1-[[[[(2-oxo-1-imidazolidinyl)carbonyl]amino]sulfonyl]amino]carbonyl]-2-oxo-3-azetidinyl]amino]-1-(2-amino-4-thiazolyl)-2-oxoethylidene]amino]oxy]-2-methylpropanoic acid, or a salt thereof.

25. The compound in accordance with claim 24: [3S(Z)]-2-[[[2-[[1-[[[[[(2-oxo-1-imidazolidinyl)carbonyl]amino]sulfonyl]amino]carbonyl]-2-oxo-3-azetidinyl]amino]-1-(2-amino-4-thiazolyl)-2-oxoethylidene]amino]oxy]-2-methylpropanoic acid, dipotassium salt.

26. A compound having the formula

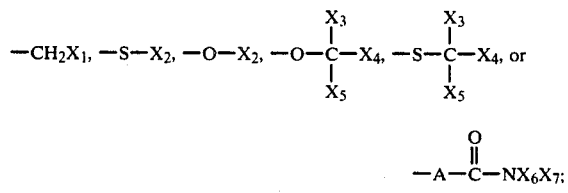

or a salt thereof wherein $R_2$ is hydrogen or methoxy;

$R_3$ and $R_4$ are the same or different and each is hydrogen, alkyl, alkenyl, alkynyl, cycloalkyl, aryl or a 5, 6 or 7-membered heterocycle or one of $R_3$ and $R_4$ is hydrogen and the other is azido, halomethyl, dihalomethyl, trihalomethyl, alkoxycarbonyl, 2-phenylethenyl, 2-phenylethynyl, carboxyl,

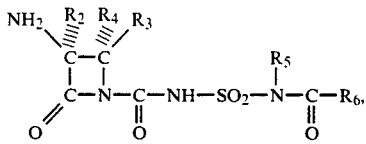

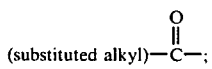

$X_1$ is azido, amino, hydroxy, alkanoylamino, alkylsulfonyloxy, arylsulfonyloxy, aryl, cyano, —S—$X_2$ or —O—$X_2$;

$X_2$ is alkyl, substituted alkyl, aryl, arylalkyl, alkanoyl, substituted alkanoyl, arylcarbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, arylcarbonyl, arylalkyl carbonyl, carboxyl, alkoxycarbonyl, aminocarbonyl, (substituted amino)carbonyl, or cyano;

A is —CH=CH—, —CH₂—CH=CH—, —(CH₂)$_m$—, —(CH₂)$_m'$—O—, —(CH₂)$_m'$—NH—, —(CH₂)$_m'$—S—CH₂—, or —(CH₂)$_m'$O—CH₂;

m is 0, 1, 2 or 3;

m' is 1 or 2;

$X_6$ and $X_7$ are the same or different and each is hydrogen or alkyl, or $X_6$ is hydrogen and $X_7$ is amino, substituted amino, acylamino or alkoxy;

$R_5$ is hydrogen, alkyl or aryl;

$R_6$ is hydrogen, alkyl, aryl, a 5, 6 or 7-membered heterocycle, —NR₇R₈, or —(CH₂)$_n$—X wherein n is 1, 2, 3 or 4 and X is halogen, aryl, alkoxy, aryloxy or —NR₉R₁₀;

$R_7$ and $R_8$ are the same or different and each is hydrogen, alkyl or aryl, or $R_7$ is hydrogen and $R_8$ is a 5, 6 or 7-membered heterocycle or —(CH₂)$_n$—Y wherein n is 1, 2, 3 or 4 and Y is alkoxy, amino, alkylthio or halogen; and $R_9$ and $R_{10}$ are the same or different and each is hydrogen or alkyl, or $R_9$ is hydrogen and $R_{10}$ is a 5, 6 or 7-membered heterocycle;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", and "alkynyl" refer to groups having 2 to 10 carbon atoms;

the term "aryl" refers to a phenyl or phenyl substituted with 1, 2 or 3 amino, halogen, hydroxyl, trifluoromethyl, alkyl of 1 to 4 carbon atoms, alkoxy of 1 to 4 carbon atoms or carboxyl groups;

the term "substituted alkyl" refers to alkyl groups substituted with one, or more, azido, amino, halogen, hydroxy, carboxy, cyano, alkoxycarbonyl, aminocarbonyl, alkanoyloxy, alkoxy, aryloxy, a 5, 6 or 7-memberd heterocycloexy, mercapto, alkylthio, arylthio, alkylsulfinyl, or alkylsulfonyl groups;

the term "substituted alkanoyl" refers to groups having the formula $$\text{(substituted alkyl)} - \overset{\overset{\text{O}}{\|}}{\text{C}} -;$$

the term "substituted amino" refers to a group having the formula —N$Y_1Y_2$ wherein $Y_1$ is hydrogen, alkyl, aryl, or arylalkyl, and $Y_2$ is alkyl, aryl, arylalkyl, hydroxy, cyano, alkoxy, phenylalkoxy, or amino;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxyazolyl, triazinyl, tetrazolyl or one of the above groups substituted with one, or more, halogen, hydroxy, nitro, amino, cyano, trifluoromethyl, alkyl of 1 to 4 carbon atoms, alkoxy of 1 to 4 carbon atoms, alkylsulfonyl, aryl, 2-furylmethyleneimino, phenylmethyleneimino or substituted alkyl, wherein the alkyl group has 1 to 4 carbon atoms, groups; and the term "a 5, 6, or 7-membered heterocycle" refers to pyridinyl, furanyl, pyrrolyl, thienyl, 1,2,3-triazolyl, 1,2,4-triazolyl, imidazolyl, thiazolyl thiadiazolyl, pyrimidinyl, oxazolyl, triazinyl, tetrazolyl, piperidinyl, piperazinyl, imidazolidinyl, oxazolidinyl, pyrrolidinyl, tetrahydropyrmidinyl, dihydrothiazolyl, or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, aryl, 2-furylmethyleneimino, phenylmethyleneimino, or substituted alkyl, wherein the alkyl group has 1 to 4 carbon atoms, groups.

* * * * *

UNITED STATES PATENT AND TRADEMARK OFFICE
CERTIFICATE OF CORRECTION

PATENT NO. : 4,670,553

DATED : June 2, 1987

INVENTOR(S) : Hermann Breuer, Theodor Denzel

It is certified that error appears in the above-identified patent and that said Letters Patent is hereby corrected as shown below:

In column 37, line 13 add --or-- after "alkyl".

Signed and Sealed this

Eighth Day of March, 1988

Attest:

DONALD J. QUIGG

Attesting Officer

Commissioner of Patents and Trademarks